US009138277B2

(12) United States Patent
Fitzpatrick

(10) Patent No.: US 9,138,277 B2
(45) Date of Patent: Sep. 22, 2015

(54) SPINAL IMPLANTS AND SPINAL FIXINGS

(75) Inventor: Noel Fitzpatrick, Godalming (GB)

(73) Assignee: Fitzbionics Limited (GB)

( * ) Notice: Subject to any disclaimer, the term of this patent is extended or adjusted under 35 U.S.C. 154(b) by 198 days.

(21) Appl. No.: 13/642,864

(22) PCT Filed: Apr. 21, 2011

(86) PCT No.: PCT/GB2011/050800
§ 371 (c)(1),
(2), (4) Date: Oct. 23, 2012

(87) PCT Pub. No.: WO2011/131994
PCT Pub. Date: Oct. 27, 2011

(65) Prior Publication Data
US 2013/0035724 A1 Feb. 7, 2013

(30) Foreign Application Priority Data
Apr. 23, 2010 (GB) .................. 1006798.1

(51) Int. Cl.
*A61B 17/70* (2006.01)
*A61B 17/86* (2006.01)
(Continued)

(52) U.S. Cl.
CPC ........... *A61B 17/8685* (2013.01); *A61B 17/686* (2013.01); *A61B 17/7002* (2013.01);
(Continued)

(58) Field of Classification Search
CPC ........... A61B 17/7002; A61B 17/7005; A61B 17/7034; A61B 17/7035
USPC .......................................... 606/265, 268, 272
See application file for complete search history.

(56) References Cited

U.S. PATENT DOCUMENTS

| 5,480,401 A | 1/1996 | Navas |
| 5,776,135 A | 7/1998 | Errico et al. |

(Continued)

FOREIGN PATENT DOCUMENTS

| DE | 43 30 837 | 9/1993 |
| DE | 299 14 192 | 11/1999 |

(Continued)

OTHER PUBLICATIONS

International Search Report, mailed Sep. 23, 2011, International Patent Application No. PCT/GB2011/050800.

(Continued)

*Primary Examiner* — Ellen C Hammond
(74) *Attorney, Agent, or Firm* — Andrus Intellectual Property Law, LLP

(57) ABSTRACT

A spinal implant comprising an elongate body insertable between adjacent vertebrae, the elongate body comprising first and second portions, the first and second portions each having an internal surface, the internal surface of the first portion facing the internal surface of the second portion in use, at least part of each internal surface of the first and second portions being threaded, the spinal implant further comprising a bolt, at least part of the bolt being externally tapered and externally threaded, the external threads of the bolt corresponding with the threads of the internal surfaces of the first and second portions, wherein the bolt is insertable between the first and second portions of the elongate body such that the external threads of the bolt engage with the internal threads of the elongate body, whereby rotation of the bolt in the threaded internal surfaces of the first and second portions causes relative movement of first and second portions away from one another.

9 Claims, 13 Drawing Sheets

(51) Int. Cl.
*A61B 17/68* (2006.01)
*A61F 2/44* (2006.01)
*A61F 2/28* (2006.01)
*A61F 2/30* (2006.01)

(52) U.S. Cl.
CPC ......... *A61B17/7005* (2013.01); *A61B 17/7032* (2013.01); *A61B 17/7034* (2013.01); *A61B 17/7035* (2013.01); *A61B 17/7037* (2013.01); *A61B 17/7041* (2013.01); *A61B 17/864* (2013.01); *A61F 2/446* (2013.01); *A61B 17/86* (2013.01); *A61F 2002/2835* (2013.01); *A61F 2002/3085* (2013.01); *A61F 2002/30217* (2013.01); *A61F 2002/30777* (2013.01)

(56) References Cited

U.S. PATENT DOCUMENTS

| | | | |
|---|---|---|---|
| 6,379,354 | B1 | 4/2002 | Rogozinski |
| 6,565,567 | B1 * | 5/2003 | Haider .................. 606/266 |
| 6,755,835 | B2 | 6/2004 | Schultheiss et al. |
| 8,226,690 | B2 * | 7/2012 | Altarac et al. .............. 606/256 |
| 2002/0072801 | A1 | 6/2002 | Michelson |
| 2002/0123752 | A1 | 9/2002 | Schultheiss et al. |
| 2003/0158552 | A1 | 8/2003 | Jeon |
| 2003/0176864 | A1 | 9/2003 | Ueyama et al. |
| 2003/0195519 | A1 | 10/2003 | Zdeblick |
| 2004/0153089 | A1 | 8/2004 | Zdeblick et al. |
| 2006/0195096 | A1 | 8/2006 | Lee et al. |
| 2006/0241600 | A1 * | 10/2006 | Ensign et al. ............... 606/61 |
| 2006/0247642 | A1 | 11/2006 | Stone et al. |
| 2007/0010819 | A1 | 1/2007 | Johnstone |
| 2007/0100341 | A1 | 5/2007 | Reglos et al. |
| 2007/0191958 | A1 * | 8/2007 | Abdou ..................... 623/17.16 |
| 2007/0233123 | A1 | 10/2007 | Ahmad et al. |
| 2007/0239159 | A1 | 10/2007 | Altarac et al. |
| 2007/0270858 | A1 | 11/2007 | Trieu et al. |
| 2007/0270972 | A1 | 11/2007 | Gordon et al. |
| 2008/0147195 | A1 | 6/2008 | Kwak et al. |
| 2008/0183220 | A1 | 7/2008 | Glazer et al. |
| 2008/0195150 | A1 | 8/2008 | Bishop |
| 2009/0171396 | A1 | 7/2009 | Baynham et al. |
| 2010/0030135 | A1 | 2/2010 | Mitchell |
| 2010/0049253 | A1 | 2/2010 | Miller |

FOREIGN PATENT DOCUMENTS

| | | |
|---|---|---|
| FR | 2 802 083 | 6/2001 |
| WO | 9938463 | 8/1999 |
| WO | 2007/117366 | 10/2007 |
| WO | 2009111632 | 9/2009 |
| WO | 2010017631 | 2/2010 |
| WO | 2010099239 | 9/2010 |

OTHER PUBLICATIONS

Search Report, date of search Nov. 4, 2010, GB Patent Application No. 1006798.1.
Search Report, date of search Nov. 5, 2010, GB Patent Application No. 1006798.1.
Search Report, date of search Jul. 26, 2012, GB Patent Application No. 1106739.4.
EP Examination report dated Feb. 6, 2015, European Application No. 11 716 641.3.

* cited by examiner

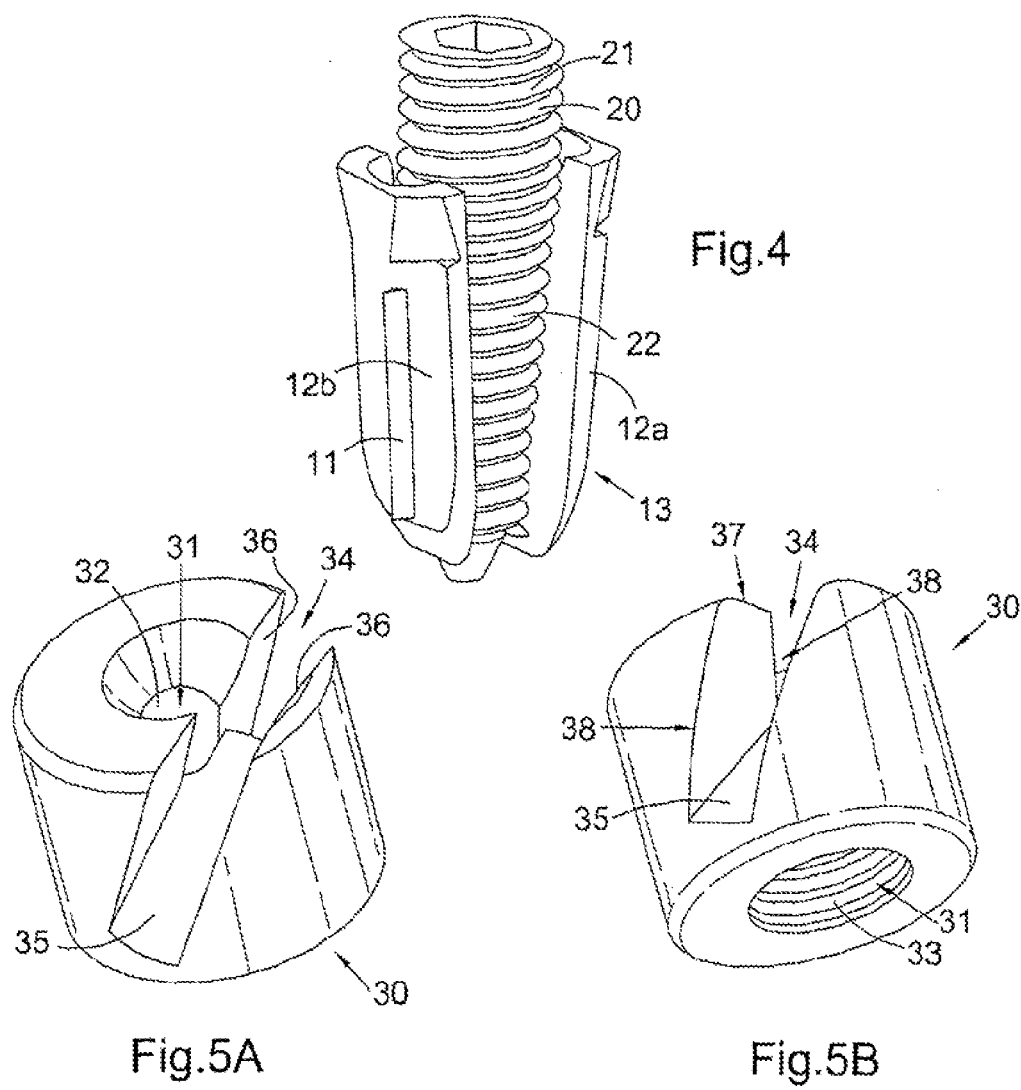
Fig.4
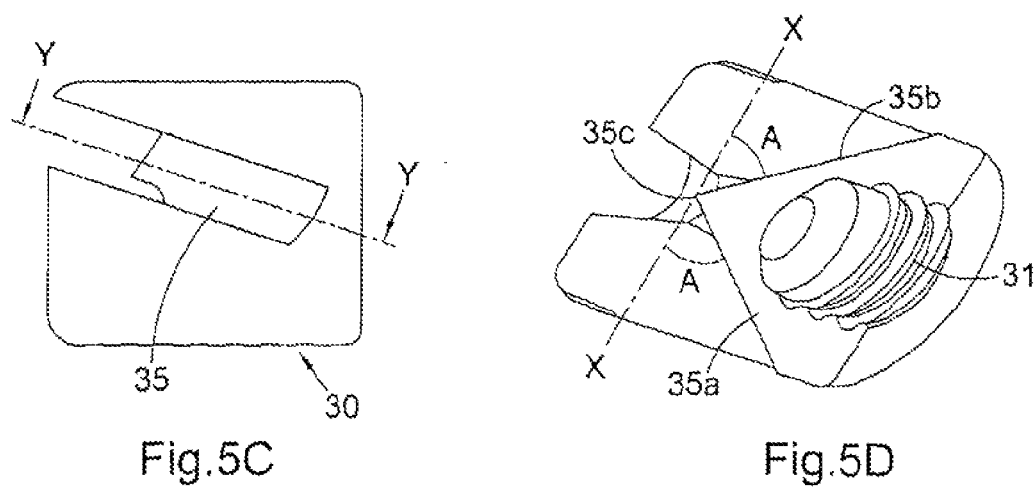
Fig.5A  Fig.5B
Fig.5C  Fig.5D

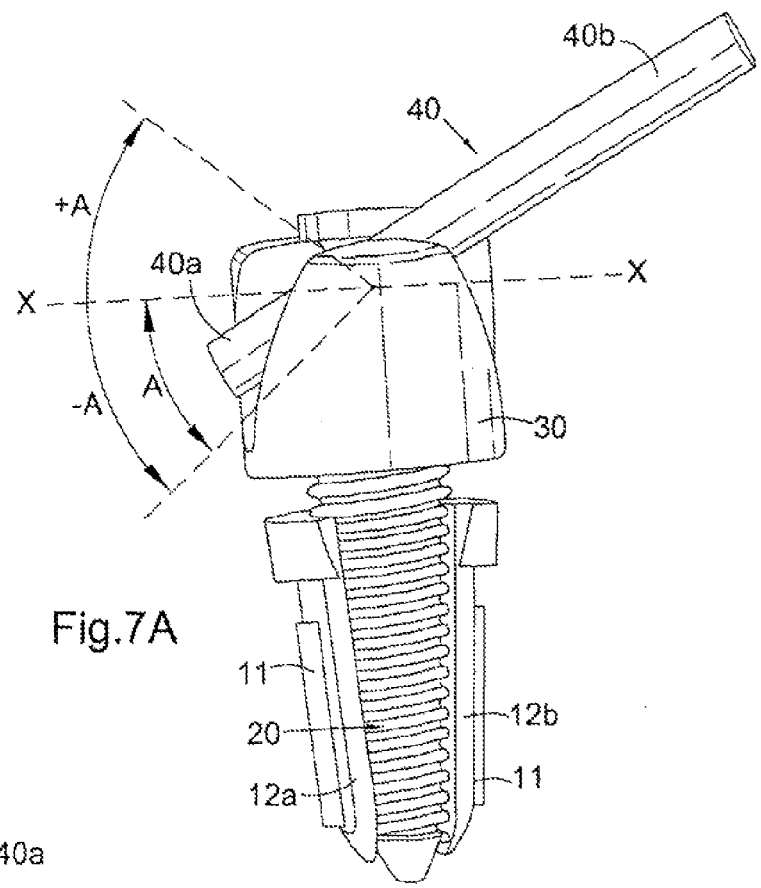
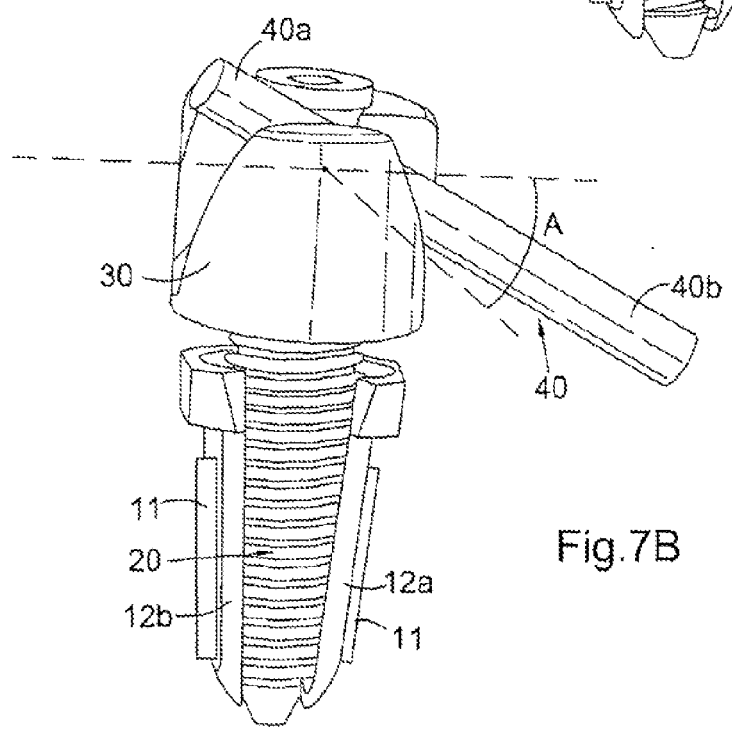
Fig.7A
Fig.7B

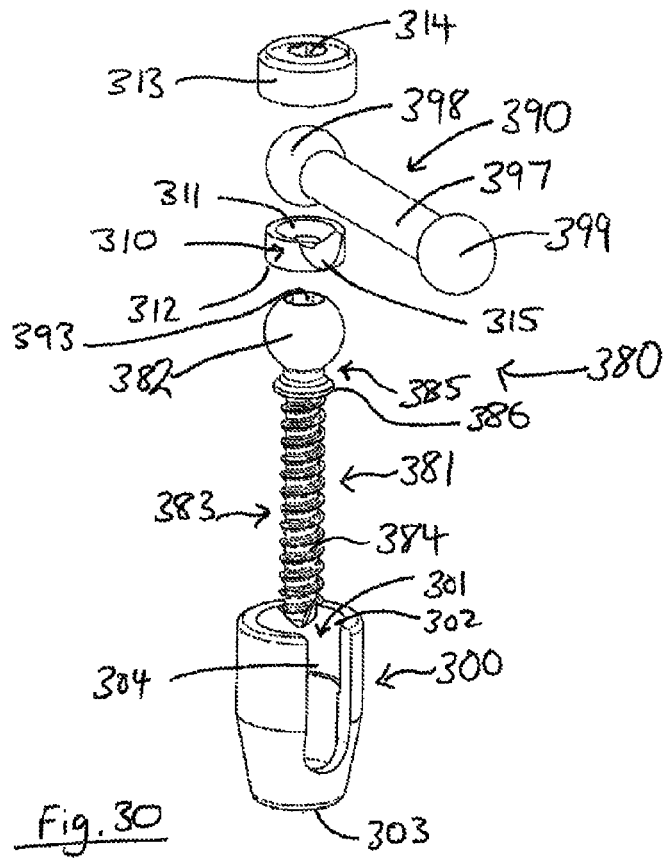
Fig. 30
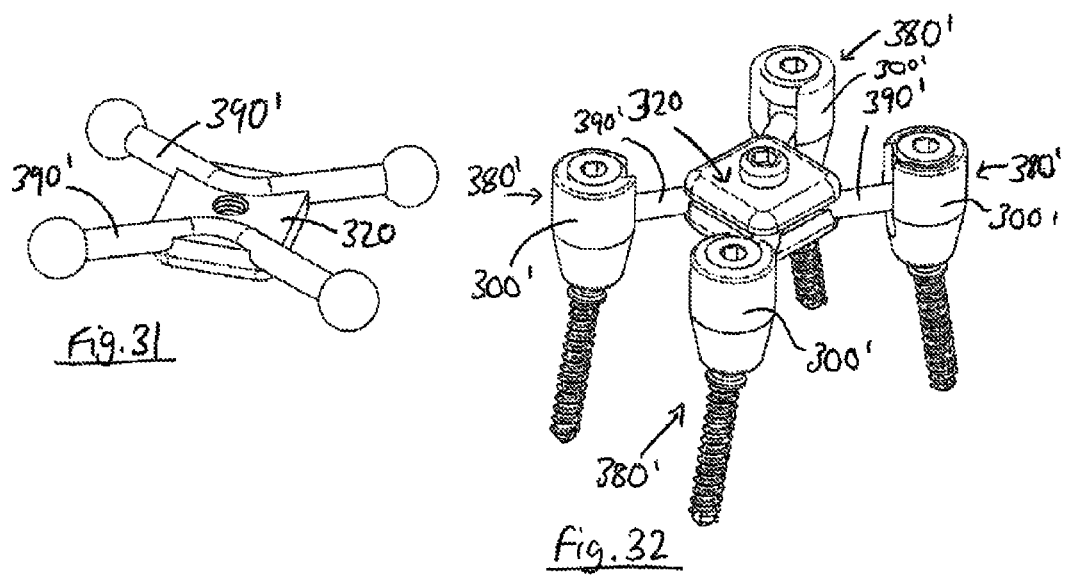
Fig. 31
Fig. 32

SPINAL IMPLANTS AND SPINAL FIXINGS

CROSS REFERENCE TO RELATED APPLICATION

The present application is the U.S. national stage application of International Application PCT/GB2011/050800, filed Apr. 21, 2011, which international application was published on Oct. 27, 2011 as International Publication WO 2011/131994. The International Application claims priority of Great Britain Patent Application 1006798.1, filed Apr. 23, 2010.

FIELD OF THE INVENTION

The invention relates to spinal/vertebral implants and spinal/vertebral fixings. Spinal implants/fixings in the form of screws or hooks are used in spinal surgery to secure elements of the spine to a support structure such as a rod, or to other spinal fixings by means of a rod or similar.

BACKGROUND TO THE INVENTION

The spine or vertebral column comprises a plurality of separate vertebrae. The vertebrae are movable relative to one another, and separated from one another by fibrocartilage called inter-vertebral discs.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve immobilization by implanting artificial assemblies in or on the spinal column.

Inter-Vertebral Disc Disease

For a patient suffering from acute inter-vertebral disc (IVD) disease, it is desirable to induce fusion and distraction of the two adjoining vertebrae, adjacent to the affected inter-vertebral disc. Inter-vertebral disc disease may particularly affect the cervical region of the spine. By distracting the two adjoining vertebrae, this relieves pressure on the spinal nerves and/or spinal cord.

Fusion cages are presently the preferred device for inducing fusion and distraction between adjoining vertebrae. Fusion devices provide a means of opening disc collapsed space between opposing vertebrae, relieving pressure on the nerves and/or spinal cord, by effectively placing a spacer in the disc space. Presently used spinal cages are generally hollow cuboid shaped devices.

Spinal Fixings

In order to treat certain injuries or conditions of the spinal column a metal rod that is bendable to match the natural curvature of the spine is mechanically attached at strategically selected vertebrae, allowing the rod to be rigidly fixed to the spine. This provides a rigid support to the spinal column. For this, screws located in the bone structure are typically fixed to a specially designed clamp to attach to a spinal rod. A problem with specially designed clamps is that bone structure cannot be determined until the patient's bone is exposed, therefore it is not known what angle the screw will need to be relative to the rod until the spinal bone structure has been examined. Certain parts of the vertabra cannot stably receive a bone screw, or can only receive a bone screw screwed in at a certain angle. Also, for spinal fixings for small animals, within the confined spaces allowed therein, conventional rod anchoring methods are not suitable since the placement of the pedicle screw and the direction of the rod cannot be matched adequately. A system that allows for easy adjustment of the alignment of a bone screw relative to a rod is needed. In particular, a system that can be used in small animals is needed, wherein confined spaces make conventional rod anchoring systems unsuitable.

Lumbo-Sacral Fusion

In vertebrates, the sacrum is a large, triangular bone at the base of the spine. The lumbo-sacral joint is a joint between the sacrum and the vertebra that is adjacent the sacrum. As between other vertebra, there is an intervertebral disc between the sacrum and the adjacent vertebra. For the purposes of this invention, the sacrum is considered to be part of the spine.

Compression of the nerves passing through the lumbo-sacral joint can occur, which is a symptom of lumbo-sacral disease.

A system for distracting the lumbo-sacral joint and stabilising the joint is needed. The bone structure of the sacrum may be soft. Perpendicular placement of a bone screw is often not possible. Therefore, there is a need for multi-axial positioning of a bone screw with respect to a stabilising rod. Many devices for providing multi-axial positioning of a bone screws with respect to a stabilising rod loosen over time, providing an unstable joint. Also, if the bone screw becomes loose, this presents forces on the fixing device, which may loosen due to the forces. There is therefore a need for a fixing device that overcomes one or more of these problems, and particularly for lumbo-sacral fusion.

SUMMARY OF INVENTION

According to a first aspect of the invention there is provided a spinal implant comprising an elongate body insertable between adjacent vertebrae, the elongate body comprising first and second portions, the first and second portions each having an internal surface, the internal surface of the first portion facing the internal surface of the second portion in use, at least part of the internal surface of each of the first and second portions being threaded, the spinal implant further comprising a bolt, at least part of the bolt being externally tapered and externally threaded, the external threads of the bolt corresponding with the threads of the internal surfaces of the first and second portions, wherein the bolt is insertable between the first and second portions of the elongate body such that the external threads of the bolt engage with the internal threads of the elongate body, whereby rotation of the bolt in the threaded internal surfaces of the first and second portions causes relative movement of the first and second portions away from one another. In this way, the bolt can wedge apart the first and second portions as the bolt is screw threaded between the first and second portions.

Preferably rotation of the bolt in the threaded internal surfaces of the first and second portions causes relative movement of the whole of the first portion away from the second portion. In other words, all parts of the first portion move away from the second portion, including both the distal and proximal ends of the first portion, as the bolt is screwed in between the first and second portions. With each turn of the bolt, the proximal end of the first portion moves further away from the proximal end of the second portion. As the bolt is rotated and screwed in, between the first and second portions, both the proximal and distal ends of each of the first and second portions moves away from the longitudinal axis of the bolt. The elongate body is adapted such that the first portion is not pivotally coupled to the second portion, nor is the first portion pivotally moveable relative to the second portion.

The elongate body can be impacted into a spinal disk between adjacent vertebrae. Suitably the outer surfaces of the first and second portions of the elongate body contact with the vertebrae when impacted. Suitably the outer surface of the first portion contacts a first vertebra and the outer surface of the second portion contacts a second vertebra. The first and second portions are distracted by insertion of the tapered bolt between the first and second portions, thus pushing apart the adjacent vertebrae and thus relieving pressure on the spinal nerve(s). Advantageously the first and second portions provide load distribution onto the underlying bone, preventing the screw from being embedded into the bone during insertion. Advantageously the first and second portions distribute distractive loads generated by the bolt when inserted, thus preventing excessive bone damage. The first and second portions also provide a guided path for insertion of the tapered screw, therefore making the distraction process controlled. By making the inner surfaces of the first and second portions congruent with the threaded bolt, this provides a guided path for the screw during insertion and for captivation. Such a device can be used for treatment of acute inter-vertebral disc disease.

Suitably, the internal surfaces of the first and second portions may be initially parallel with one another during initial implantation of the elongate body, but once the bolt is inserted, the internal surfaces are wedged apart such that the distal ends of the first and second portions are spaced apart from one another more than the proximal ends. The first and second portions of the elongate body may be externally tapered such that the elongate body is wedge shaped before insertion of the bolt; when the bolt is inserted, the external surfaces of the first and second portions are further wedged part. In this way the elongate body expands the bone before the bolt is installed, and compacts the adjacent tissue to a certain degree. This may provide more space for the bolt to be inserted into. Suitably the first and second portions of the elongate body can be externally tapered to match the taper of the bolt.

Suitably, the bolt causes distraction of the opposing vertebrae, the bolt remaining implanted in the body after the opposing vertebrae have been distracted. This is different from use of a separate distraction tool to distract vertebrae, wherein the distraction tool is removed and does not remain implanted in the body after distraction of the opposition vertebrae. By using a screw threaded bolt which engages in screw threads on the elongate body to wedge apart the portions of the elongate body, the bolt is held securely between the first and second portions of the elongate body (which are rigidly held to the bone), the bolt forming a stable support for attachment of a rod, such as a spinal rod.

Preferably the bolt has a proximal end and a distal end and the external taper of the bolt tapers towards the proximal end of the bolt.

In this context the term proximal used in relation to parts of spinal implants or spinal fixings means located nearer or towards the centre of the subject's body or spine when the implant part or fixing part is installed and distal means located away from the centre of the body or spine when the implant part or fixing part is installed.

The term subject as used herein can be a human or animal subject.

Preferably the bolt has a non-tapered portion at its distal end and a tapered portion at its proximal end.

Preferably the bolt is longer than the elongate body, the distal end of the bolt protruding from the elongate body when the bolt is fully inserted between the first and second portions of the elongate body.

Preferably the implant further comprises a rod supporting body at the distal end of the bolt in use, the rod supporting body having a groove for receiving a rod. For example, the groove may receive a spinal rod.

The rod can be used to couple together two spinal implants according to the present invention, helping to stabilise each of the implants; or the rod can be for connecting a spinal implant to another type of spinal implant. The rod can be straight or bendable. Existing fusion cages of the art do not include means for interconnection with other fusion cages.

Preferably the rod supporting body is releasably coupled to the bolt in use. Preferably the rod supporting body is rotatable relative to the bolt in use. Preferably the spinal implant further comprises locking means, for preventing rotation of the rod supporting body relative to the body.

Preferably the rod supporting body has a bore connecting first and second open ends, at least part of the bore of the rod supporting body being internally threaded, the internal threads of the bore corresponding with the external threads of a non-tapered portion of the distal end of the bolt, such that the rod supporting body is rotatable on the bolt when assembled thereto. The body can be loosely screwed onto the bolt so that it can rotate for alignment with a spinal rod or rod anchored to the bone. This allows the rod supporting body to be rotated optimally to align with a rod.

Preferably the groove of the rod supporting body has a base, two side walls, a top opening and two side openings, the base having first and second faces inclining towards an apical centre-line.

Preferably the groove is substantially triangular in shape, the first and second faces of the base inclining towards the apical centre-line. Preferably the first and second faces are planar.

Alternatively the base of the groove may be convexly curved.

Preferably the first and second faces of the base of the groove are inclined such that the angular alignment of the longitudinal axis of a rod with respect to the longitudinal axis of the bolt can be varied by pivoting the rod about the apical centre-line of the base. In other words, the rod can pivot about the apical centre-line of the base, like a see-saw.

Preferably the longitudinal axis of the rod can be varied between an angle −A and an angle +A relative to a reference line, the reference line being perpendicular to the longitudinal axis of the bolt in use, the angle between the first face and the reference line being angle A and the angle between the second face and the reference line being angle A. The longitudinal axis of the rod can be varied between a continuous range of angles between an angle −A and an angle +A relative to a reference line. Suitably the rod can aligned at a range of angles relative to the bolt, depending on where another part of the rod is fixed or needs to be fixed.

Preferably the longitudinal axis of the rod can be varied between an angle −40° and an angle +40° relative to a reference line. The triangulated base support for the rod allows the rod to be misaligned by up to 40° in either direction relative to the reference line. The inclined groove with triangulated base allows the rod to rest on the pinnacle of the triangle allowing up to 40° of angulation up or down.

Suitably the spinal implant provides rod misalignment from any direction with elevational misalignment.

Preferably the side walls of the groove are parallel with one another. Preferably the side walls of the groove are substantially planar.

Preferably the spinal implant further comprises a locking screw, the locking screw having a shank, at least part of the shank being externally threaded, the bolt having a bore with a first open end, the bore being internally threaded, the internal threads of the bolt corresponding with the external threads of the shank of the locking screw, the rod supporting body having a bore connecting first and second open ends, the screw being receivable in the bore of the rod supporting body and threadedly receivable in the bore of the bolt. Suitably the locking screw can be threadedly engaged in the bore of the bolt with the rod supporting body between the screw head and the bolt, thus locking the rod supporting body onto the bolt.

Preferably the locking screw has a head, the head overlying at least part of the groove when the locking screw is assembled with the rod supporting body and bolt, such that a rod inserted in the groove cannot be removed from top opening of the groove when the locking screw is assembled with the rod supporting body and bolt.

Preferably the screw head has an underside having a tapered portion, the tapered portion tapering towards the screw shank.

Preferably the angle of taper of the tapered portion of the screw head relative to a reference line, the reference line being perpendicular to the longitudinal axis of the bolt when the screw is installed is substantially the same as angle A, or is a few degrees greater than angle A. This creates a holding pressure and a tightening force on the rod between the tapered portion of the screw and the rod supporting body.

Preferably the first open end of the bore of the rod supporting body is countersunk. This balances the holding pressure exerted by the tapered portion of the screw on the rod. The countersunk open end of the rod supporting body is a conical recess in the top of the rod supporting body in use, the conical recess preferably being elongated to allow pressurisation on the rod to take place.

Preferably at least part of the outer surface of the elongate body is hydroxyapatite coated. This promotes bone in-growth with the outer surface of the elongate body. Preferably at least part of the outer surface of the elongate body is porous. Such surface treatments stimulate bone integration over time.

Preferably at least part of the outer surface of the elongate body includes fixation means for fixing the elongate body to vertebrae. The fixation means may comprise serrations, fins or threaded surface to dig into the bony surface of the corresponding vertebra. This provides mechanical stability during insertion.

According to a second aspect of the invention there is provided a kit comprising a first spinal implant according to the first aspect of the invention, the kit further comprising a spinal rod.

Preferably the kit may further comprise a second spinal implant according to the first aspect of the invention.

According to a third aspect of the invention there is provided a method of installing a spinal implant according to the first aspect of the invention, the method comprising the steps of:
 providing a spinal implant according to the first aspect of the invention;
 implanting the elongate body between adjacent vertebrae;
 threadably inserting the bolt between the first and second portions of the elongate body to wedge apart the first and second portions as the bolt is screw threaded between the first and second portions.

According to a fourth aspect of the invention there is provided a spinal implant comprising a fixing part for fixing to a part of a subject's spine, the spinal implant further comprising a rod supporting body at the distal end of the fixing part in use, the rod supporting body having a groove for receiving a rod, the groove having a base, two side walls, a top opening and two side openings, the base having first and second faces inclining towards an apical centre-line. Preferably the groove is substantially triangular in shape, the first and second faces of the base inclining towards the apical centre-line. Preferably the rod supporting body is rotatable on the body when assembled thereto.

According to a fifth aspect of the invention there is provided a vertebral fixing comprising a fixing part for fixing to a part of a subject's spine, a rod supporting component for supporting a rod, and a coupling body for coupling the fixing part and the rod supporting component, the rod supporting component being rotatably coupleable to the coupling body.

The rotatable coupling of the rod supporting component with the coupling body allows for rotational adjustment of the rod supporting component relative to the coupling body. The vertebral fixing can optionally have means for rotatably fixing the rod supporting component relative to the coupling body once the desired rotational alignment of the rod supporting component relative to the coupling body has been achieved.

Suitably the rod supporting component supports, receives or couples to a rod such as a spinal rod. Suitably the rod supporting component has rod receiving means for receiving a rod.

Several vertebral fixings according to the invention can be fixedly coupled, each at different locations on a subject's spine, and each supporting a single metal spinal rod at different locations on the rod. The rod supporting component can be rotated relative to the coupling body and relative to the fixing part, to align a rod receiving means of the rod supporting component such that the rod receiving means is aligned along a suitable axis for receiving the rod (which may be coupled to the subject's spine already at one or more points by one or more vertebral fixings), once the fixing part has been fixed to the subject's bone. Therefore, even if the fixing part cannot be fixed with its longitudinal axis perpendicular to the longitudinal axis of the rod, because the subject's bone will not allow the fixing part to be fixed in that alignment, the rod supporting component can be rotated relative to the coupling body and to the fixing part to align with the rod.

Preferably the rod supporting component can be arranged such that the rod supporting component is captively retained to the coupling body and wherein the rod supporting component is movable relative to the coupling body, while remaining captive to the coupling body in use. This arrangement can be used during installation of the vertebral fixing, to allow the rod supporting component to be rotated relative to the coupling body to a desired alignment.

Preferably the rod supporting component can be arranged such that the rod supporting component is captively retained to the coupling body and wherein the rod supporting component is rotatable and/or configured to translate relative to the coupling body, while remaining captive to the coupling body in use.

Preferably the vertebral fixing is convertible between a first configuration in which the rod supporting component is captively retained to the coupling body and wherein the rod supporting component moveable relative to the coupling body while remaining captive to the coupling body in use, and a second configuration in which the rod supporting component is non-moveable relative to the coupling body. Suitably, the first configuration is used during installation of the vertebral fixing, in order that the rod supporting component can be adjusted to a desired orientation relative to the coupling body. The rod supporting component can then be converted to the second configuration once the desired alignment of the rod relative to the coupling body has been achieved, locking the alignment of the rod supporting component relative to the coupling body.

Preferably the rod supporting component has a channel for receiving a rod, the channel having first and second open ends and a longitudinal opening between the first and second open ends. Suitably the channel is an open channel into which the rod can be top loaded (i.e. a mid portion of the rod can be directly inserted in the channel, without needing to feed a rod end through the first or second open end of the channel).

Preferably the rod supporting component is arranged such that when the vertebral fixing is in the second configuration the rod supporting component is non-movably coupled in relation to the coupling body such that part of the coupling body obstructs at least part of the longitudinal opening of the channel. Suitably, this prevents any rod received in the channel from being removed from the channel when the rod supporting component is non-movably fixed relative to the coupling body. In this locked configuration, the coupling body pushes against a rod received in the channel, rigidly fixing the rod to the rod supporting component.

Preferably the channel is formed in a hook. Preferably the hook has a hooked end, the hooked end extending parallel to the axis of the shaft in a retrograde manner.

Preferably the rod supporting component has a groove. Suitably, the groove is on a shaft that is received within a bore of the coupling body. Suitably, the groove encircles the shaft.

Preferably the vertebral fixing further comprises a retention pin coupling the coupling together body and the rod supporting component in use, the retention pin being received in the groove in use, such that the rod supporting component is captively retained to the coupling body and wherein the rod supporting component may be movable relative to the coupling body, while remaining captive to the coupling body in use.

Preferably the vertebral fixing further comprises means for non-movably clamping the rod supporting component to the coupling body. Preferably such means comprises a first screw for non-movably clamping the rod supporting component to the coupling body. Preferably such means may comprise first and second screws for non-movably clamping the rod supporting component to the coupling body. Preferably the coupling body has a first threaded bore, the screw being threadedly receivable in the threaded bore and a groove in the rod supporting component, such that tightening of the screw within the threaded bore rigidly fixes the rod supporting component to the coupling body. Suitably, tightening of the screw also prevents a rod received in the channel from being removed from the channel.

Preferably the fixing part has a head portion and an extension portion, the head portion being pivotally coupled to the coupling body in use, such that the extension portion can pivot relative to the coupling body over a pre-determined range of motion. Therefore, even if the fixing part cannot be fixed to the patient's bone such that the extension portion extends at the desired angle relative to the axis of the spinal rod, the coupling body can be pivoted relative to the axis of the extension portion. The vertebral fixing provides a large range of angular misalignment between the fixing part and the rod.

Preferably the coupling body has a bore for receiving the fixing part, the bore having a shoulder, the extension portion of the fixing part being insertable through the bore, the head portion engaging the shoulder in use.

Preferably the shoulder has a rounded surface, the head portion having a rounded underside corresponding to the rounded surface of the shoulder. The rounded part of the head portion can pivot relative to the rounded surface of the shoulder, allowing the coupling body to pivot relative to the fixing part when assembled.

Preferably the bore for receiving the fixing part has a first open end, the first open end being funnel shaped to serve as a limiter to permit the extension portion to pivot relative to the coupling body to a limited degree. The extension portion can pivot relative to the coupling body by up to a pre-determined angle, defined by the funnel shaped open end, in any direction.

Preferably the rod supporting component has a shaft and the coupling body has a bore for rotatably receiving the shaft. Suitably the longitudinal axis of the bore for receiving the shaft is perpendicular to the longitudinal axis of the bore for receiving the fixing part.

In one embodiment, the shaft of the rod supporting component is externally threaded, the vertebral fixing further comprising a nut having an internally threaded bore, the shaft being receivable in the bore of the nut. The nut can be used to retain the coupling body on the shaft of the rod supporting component. In this embodiment, the shaft of the rod supporting component is received in the corresponding bores of the coupling body and the nut in use, the coupling body being between the nut and a rod supported by the rod supporting component in use, such that tightening of the nut against the coupling body pushes the coupling body against the rod, rigidly fixing the rod to the rod supporting component. Suitably, tightening of the nut rigidly fixes the rod supporting body to the coupling body, and rigidly fixes the rod to the rod supporting component.

Preferably the fixing part comprises a screw for anchoring to bone or a hook that can be fixed to bone.

According to a sixth aspect of the invention there is provided a spinal fixing comprising a fixing part for fixing to a part of a subject's spine, the fixing part having a first end, the first end having a head that is at least partially spherical;

an elongate extension, the elongate extension having a first end, the first end having a head that is at least partially spherical;

a coupling body for receiving the first end of the fixing part and the first end of the elongate extension therein; and a washer for location between the first end of the fixing part and the first end of the elongate extension in use.

The washer provides a greater contact for the at least partially spherical heads of the fixing part and elongate extension to contact with, than simply contact between the at least partially spherical first ends of the fixing part and elongate extension. The washer provides improved contact for providing a rigid sustainable joint, once the elongate extension and fixing part are compressed together by a compression member, for locking the elongate extension and fixing part against pivotal movement relative to the coupling body. In devices where at least partially spherical heads contact each other during pivotal movement relative to one another, there are often problems due to erosion and/or fretting of the surface heads. If the heads are eroded/fretted, when the fixing is locked by a compression member, it can be difficult to rigidly lock the articulation of the fixing, as the heads will tend to loosen from contact with one another due to the erosion/fretting on the surface. The washer also distributes loads evenly between the fixing part and elongate extension. Such a fixing can be used in particular for stabilising the lumbo-sacral joint.

Suitably, the washer is substantially rigid and is not intended to deform when the at least part spherical ends of the fixing part and/or elongate extension are being inserted in the corresponding sockets of the washer.

Preferably the washer has first and second opposing surfaces, the first and second surfaces being concavely curved.

Preferably the washer has first and second opposing surfaces, the first surface being concavely curved, the first surface facing the first end of the elongate extension in use, the radius of curvature of the first surface being smaller than the radius of curvature of the at least partially spherical end of the elongate extension. Suitably, the radius of curvature of the first surface of the washer is only smaller than that of the elongate extension by a small amount, but sufficient such as to provide edge contact between an edge of the first surface and the first end of the elongate extension. The line of contact between the washer and the first end of the elongate extension is a circular line of contact around the at least partially spherical end of the elongate extension.

Preferably the washer has first and second opposing surfaces, the second surface being concavely curved, the second surface facing the first end of the fixing part in use, the radius of curvature of the first surface being smaller than the radius of curvature of the at least partially spherical end of the fixing part. Suitably, this provides a circular line of contact between the washer and first end of the fixing part, as with the engagement between the washer and the first end of the elongate extension.

Suitably the head of the first end of the elongate extension has the same diameter as the head of the first end of the fixing part.

Suitably the elongate extension may have a second end, the second end having a head that is at least partially spherical. The second end is for coupling with a bone-anchored fixing part, using a second spinal fixing according to the present invention.

Preferably the spinal fixing further comprises a compression member for compressing the first end of the fixing part and the first end of the elongate extension in locking engagement within the coupling body. Suitably, when the compression member locks the first end of the fixing part and the first end of the elongate extension in locking engagement within the coupling body, the fixing part and elongate extension cannot pivot relative to one another or relative to the coupling body.

Preferably the compression member is a locking screw. Preferably at least part of the locking screw is externally threaded, the coupling body having a bore with first and second open ends, at least part of the bore being internally threaded, the internal threads of the bore corresponding with the external threads of the locking screw.

Preferably the coupling body comprises a hollow tubular body, the first end of the fixing part and the first end of the elongate extension being receivable in the hollow tubular body in use.

Preferably the first end of the fixing part is pivotally coupled to the coupling body in use, such that the fixing part can pivot relative to the coupling body over a pre-determined range of motion. Suitably the fixing part can pivot relative to the coupling body by up to 25° in any direction.

Preferably the coupling body has a slot, the elongate extension extending through the slot in use, such that the elongate extension can pivot relative to the coupling body over a pre-determined range of motion. Suitably the elongate extension can pivot in the plane of the slot by up to 25° in either direction within the plane.

Preferably the slot is elongate, having a longitudinal axis parallel with the longitudinal axis of a bore of the coupling body. Suitably the slot is open at one end and communicates with an open end of the bore.

In one embodiment, the first end of the fixing part comprises a part-spherical head part and a removable rocker, the part-spherical head part being integral with or rigidly fixed to the fixing part, the rocker having first and second opposing surfaces, the first surface being part-spherical, the rocker having a male protrusion projecting from the second surface, the part-spherical head having a female recess for receiving the male protrusion. Suitably, the part-spherical head and removable rocker form the at least partially spherical end of the fixing part, when assembled. More preferably, the part-spherical head and removable rocker form a substantially complete spherical head when assembled. The term part-spherical as used herein refers to a surface that comprises a portion of a sphere. Advantageously, a torque-providing tool can be engaged in the female recess to drive the fixing part into a subject's bone, after which the rocker can be placed on the part-spherical head part to form a complete spherical head to the fixing part.

In one embodiment, the washer has first and second opposing surfaces, the first and second surfaces being concavely curved, the curvature of the first and second surfaces corresponding with the curvature of the first end of the fixing part and the first end of the elongate extension respectively. Suitably, conforming surfaces between the head of the fixing part and the coupling body and between the head of the fixing part and the washer provides improved surface contact, providing a rigid sustainable joint. Similarly, conforming surfaces between the head of the elongate extension and the coupling body and between the head of the elongate extension and a compression member forms a rigid and stable interface.

According to a seventh aspect of the invention there is provided a bone screw for anchoring to a bone, the bone screw having a first end having a head that is at least partially spherical, the first end of the bone screw comprising a part-spherical head part and a removable rocker, the part-spherical head part being integral with or rigidly fixed to the fixing part, the rocker having first and second opposing surfaces, the first surface being part-spherical, the rocker having a male protrusion projecting from the second surface, the part-spherical head having a female recess for receiving the male protrusion.

Further aspects of the sixth and seventh inventions will now be summarised.

Preferably the first surface of the rocker is substantially hemispherical. Preferably the part-spherical head part has a first surface and a second surface, the first surface being substantially hemispherical and the female recess being located in the second surface.

Preferably the fixing comprises a bone screw for anchoring to bone, at least part of the bone screw being externally threaded.

According to an eighth aspect of the invention there is provided a kit comprising a spinal fixing according to the fifth aspect of the invention and a tapered bolt, the tapered bolt being externally threaded and having a hollow bore. Suitably, the bolt can be impacted at the lumbo-sacral joint between the sacrum and adjacent vertebra, to distract the lumbo-sacral joint before using spinal fixings to stabilise the joint Preferably the tapered bolt has at least one elongate slot, the elongate slot communicating with the hollow bore. Suitably, the elongated slot allows for insertion of bone graft.

According to a ninth aspect of the invention there is provided a bolt for insertion in a bone, the bolt being tapered, externally threaded and having a hollow bore, the bolt further comprising at least one elongate slot, the elongate slot communicating with the hollow bore. Suitably, the bolt can be impacted at the lumbo-sacral joint between the sacrum and adjacent vertebra, to distract the lumbo-sacral joint before using spinal fixings to stabilise the joint The bolt is a vertebral distraction bolt for insertion between vertebrae or at the lumbo-sacral joint.

Preferably at least part of the bolt is hydroxyapatite coated.

According to a tenth aspect of the invention, there is provided a vertebral distraction bolt assembly comprising a bolt according to the ninth aspect of the invention, the bolt comprising first and second elongate slots, the assembly further comprising a rod, insertable through the first and second elongate slots to anchor the bolt to bone in use.

According to an eleventh aspect of the invention, there is provided a hydroxyapatite coating for use in coating a vertebral distraction bolt for insertion between vertebrae or insertion at the lumbo-sacral joint, the bolt being tapered, externally threaded and having a hollow bore, the bolt further comprising at least one elongate slot, the elongate slot communicating with the hollow bore.

According to a twelfth aspect of the invention there is provided a kit comprising at least one spinal implant according to the first aspect of the invention, at least one vertebral fixing according to the third aspect of the invention and a spinal rod.

According to a thirteenth aspect of the invention, there is provided a method of installing a vertebral distraction bolt according to the ninth aspect of the invention, the method comprising the steps of:
providing a vertebral distraction bolt according to ninth aspect of the invention;
implanting the bolt between adjacent vertebrae or at between a vertabra and the sacrum.

According to a further aspect of the invention there is provided a method of installing a vertebral distraction bolt assembly according to the tenth aspect of the invention, the method comprising the steps of:
providing a vertebral distraction bolt assembly according to the tenth aspect of the invention;
implanting the bolt between adjacent vertebrae or at between a vertabra and the sacrum;
inserting the rod through the first and second elongate slots to anchor the bolt to bone.

BRIEF DESCRIPTION OF THE DRAWINGS

A preferred embodiment of the present invention will now be more particularly described by way of example only with reference to the accompanying drawings, wherein:

FIG. 4 is a side perspective view of the bolt and elongate body of a spinal implant of FIG. 1, with the bolt inserted in the elongate body;

FIGS. 5A and 5B are top and bottom perspective views of the rod supporting body of a spinal implant of FIG. 1; FIG. 5C is a side view of the rod supporting body of FIGS. 5A and 5B and FIG. 5D is a cross-sectional view through the plane Y-Y, as shown in FIG. 5C;

FIGS. 7A and 7B are side views of a spinal implant of FIG. 1, each with a spinal rod coupled thereto, at minimum and maximum angular alignments relative to a reference line respectively;

FIGS. 8 to 11 and 21 show another embodiment;

FIG. 8 is a top perspective view of an embodiment of a vertebral fixing assembled together for use;

FIG. 9 is a bottom perspective view of the vertebral fixing of FIG. 8;

FIG. 10 is a side perspective view of the rod supporting component of the vertebral fixing of FIG. 8;

FIGS. 12 to 18 show another embodiment;

FIG. 12 is a side perspective view of an embodiment of a spinal fixing assembled together for use;

FIG. 13 is a bottom perspective view of the spinal fixing of FIG. 12;

FIG. 14 is an exploded perspective view of the fixing part of the spinal fixing of FIG. 12;

FIG. 15 is a perspective view of the fixing part, washer and elongate extension of the spinal fixing of FIG. 12, with the elongate extension exploded from the other components;

FIG. 16 is a perspective view of the fixing part, washer and coupling body of the spinal fixing of FIG. 12, assembled together;

FIG. 17 is a cross-sectional view through the spinal fixing of FIG. 12;

FIG. 19 is a side view of a tapered bolt, particularly useful for insertion at the lumbo-sacral joint;

FIG. 20 is a cross-sectional view of a tapered bolt similar to the tapered bolt of FIG. 19, inserted at the lumbo-sacral joint;

FIG. 21 shows a cross-sectional view through the plane Z-Z, as shown in FIG. 8;

FIGS. 22 to 27 show another embodiment, similar to that of FIGS. 8 to 11 and 21, but wherein the rod supporting component can be captively held within the coupling body, yet still position adjustable with respect to the coupling body for the purposes of adjustment during installation;

FIG. 22 shows a top perspective view of an alternative embodiment of a vertebral fixing assembled together for use;

FIG. 23 is a bottom perspective view of the vertebral fixing of FIG. 22;

FIG. 26 shows a cross-sectional view through the plane A-A, as shown in FIG. 22;

FIG. 27 is a perspective view of the coupling body of the vertebral fixing as in FIG. 25B, but showing mirror plane C-C;

FIGS. 28 to 32 show another embodiment, similar to that of FIGS. 12 to 18, but having a different washer and the spinal fixing not including a separable rocker;

FIG. 28 is a cross-sectional view through an alternative embodiment of an assembled spinal fixing;

FIG. 29 is a perspective view of the fixing part, washer and coupling body of the spinal fixing of FIG. 28, assembled together;

FIG. 30 is an exploded view of the fixing part, washer and coupling body of the spinal fixing of FIG. 28;

FIG. 31 shows a close-up view of the linker block without its cover, similar to that shown in FIG. 18A;

FIG. 32 is a perspective view of four spinal fixings of the type shown in FIG. 28 linked by two rods and a linker block of FIG. 31.

DESCRIPTION OF THE PREFERRED EMBODIMENTS

The present embodiments represent currently the best ways known to the applicant of putting the invention into practice. But they are not the only ways in which this can be achieved. They are illustrated, and they will now be described, by way of example only.

Figure 1:
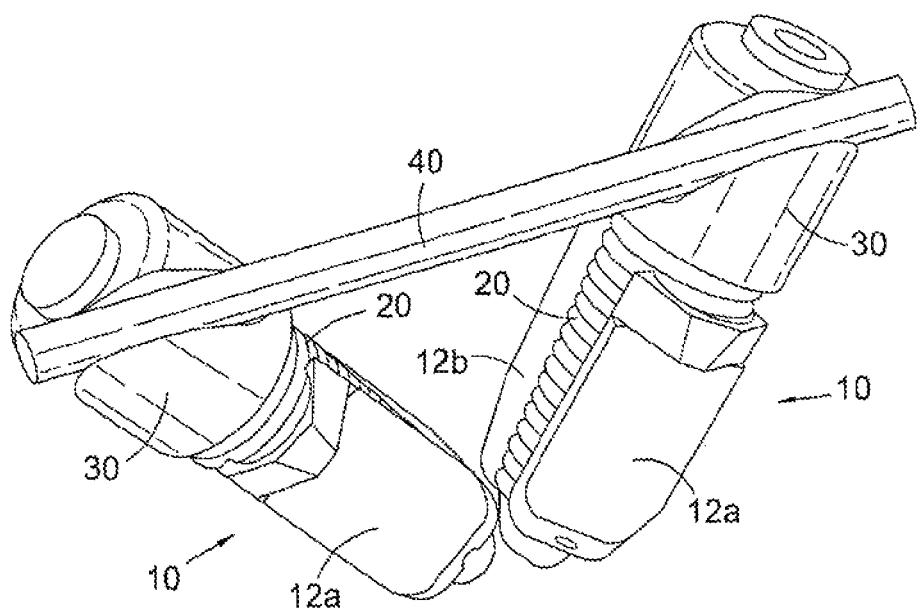
FIG. 1 is a side perspective view of a two spinal implants according to the first aspect of the invention, the two spinal implants shown coupled by a spinal rod.

Referring to FIG. 1, this shows first and second spinal implants 10 coupled to one another by a spinal rod 40. The spinal implant 10 is useful in particular for treatment of acute inter-vertebral disc disease. The rod is shown in FIG. 1 as straight, however the rod can be a bendable spinal rod.

Figure 2:
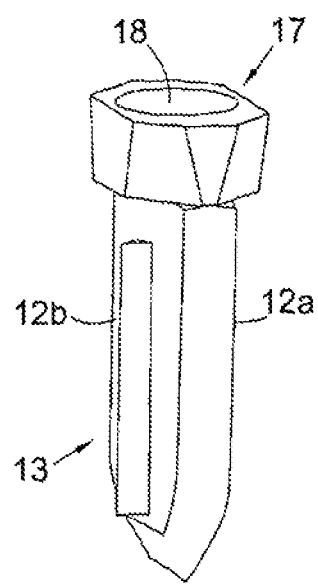
FIG. 2 is a side perspective view of the elongate body of a spinal implant of FIG. 1.
Figure 3:
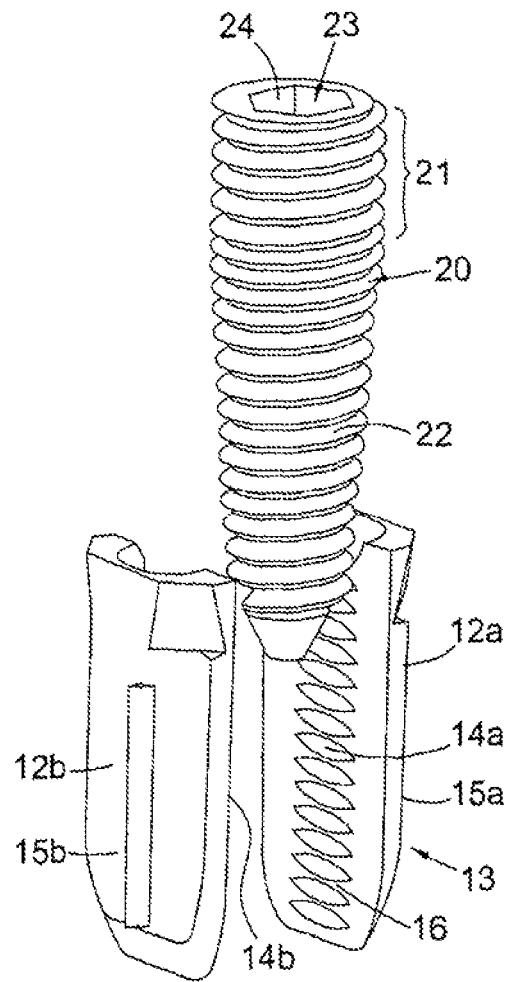
FIG. 3 is an exploded side perspective view of the bolt and elongate body of a spinal implant of FIG. 1, during insertion of the bolt in the elongate body.

Referring to FIGS. 1 and 2, a spinal implant comprises an elongate body 13 comprising first and second portions or plates 12a,12b. Referring to FIG. 2, this shows the elongate body ready for implantation in the spine. Referring to FIG. 3, the first and second plates 12a, 12b are identical, and have internal surfaces 14a,14b at least part of which abut one another when the first and second plates 12a, 12b are aligned ready for implantation. When aligned ready for implantation, the first and second plates 12a, 12b form an elongate body 13 that is thin enough to be impacted into the spinal disc.

The elongate body 13 has a proximal end and a distal end. The distal end of the elongate body 13 has an enlarged head 17, having an opening 18 for receiving the proximal end of a bolt 20. The head 17 of the elongate body 13 is hexagonal in cross-sectional shape in a plane transverse to the longitudinal axis of the elongate body. The hexagonal shaped head 17 is receivable in a corresponding hexagonal shaped bore of an insertion tool or can be gripped by collet fingers of an insertion tool (not shown in the figures) for use in holding the first and second portions together during installation, and impacting the elongate body between opposing vertebrae. It will be understood that the elongate body could be divided into more than just the first and second elongate plates, but could, for example, be formed from three separate, elongate plates.

The outer surfaces of the first and second plates 12a,12b contact with opposing vertebrae once implanted. Preferably the outer surfaces 15a,15b of the first and second plates 12a,12b have fixation means for fixing the elongate body to vertebrae. Such fixation means may comprise serrations, fins or a threaded surface, to dig into the bony surface of the corresponding vertebra. This forms an interlock with the bone during insertion of the elongate body 12. In the embodiment of FIGS. 1 to 7, the first and second plates 12a,12b each have an elongate fin 11 (visible in FIGS. 6, 7A and 7B) projecting from the outer surface, each fin having a longitudinal axis parallel with that of the respective elongate plates 12a,12b.

The outer surfaces 15a,15b of the first and second plates may be shot blasted, to give them a porous outer surface and/or coated with hydroxyapatite, to stimulate bone in-growth with the plates over time.

Each of the internal surfaces 14a,14b of the plates has a threaded portion 16 (the threaded portion of second plate 14b is not visible in FIG. 3). The spinal implant further comprises a bolt 20. The bolt has a distal end and a proximal end, the proximal end being configured for insertion into the elongate body 13. The bolt has a distal portion 21, the distal portion being non-tapered, and a proximal portion 22, the proximal portion tapering towards the proximal end of the bolt. Both the distal portion 21 and the proximal portion 22 are externally threaded. The external thread of the proximal portion 22 corresponds with the internal thread of the threaded portion 16 of each of the internal surfaces 14a,14b of the plates 12a,12b. In this way, when the bolt 20 is screwed in between the first and second plates 12a, 12b, the external threads of the proximal portion 22 of the bolt engage with the threaded portion 16 of each of the plates 12a,12b. As the bolt 20 is screwed in between the first and second plates 12a, 12b, it forces the plates apart, thus relieving pressure on any entrapped nerve(s).

The bolt 20 has a bore 23 having a first open end 24 in the distal end of the bolt. The first open end 24 of the bore 23 is hexagonal in shape, allowing a hexagonal shaped key tool to be used to screw the bolt 20 between the first and second portions.

The bolt 20 is longer than the elongate body 13. Referring to FIG. 4, when the bolt 20 is fully inserted in the elongate body 13 (such that the proximal end of the external threading of the proximal portion 22 of the bolt has engaged with the proximal end of the thread of the threaded portion of each of the internal surfaces 14a,14b of the plates 12a,12b) the distal portion 21 of the bolt protrudes from the elongate body 13.

Referring to FIGS. 5A-5D and 6, the spinal implant further includes a cap or body 30 for supporting a rod. The body 30 is generally cylindrical in shape. The body 30 has a central bore 31 connecting first and second open ends 32, 33. The bore 31 is internally threaded, the internal threads of the bore corresponding with the external threads of the distal portion 21 of the bolt 20. The body 30 is releasably coupleable to the bolt 20 by means of threaded engagement of the body 30 on the distal portion 21 of the bolt 20. When the body 30 is received on the distal portion 21 of the bolt 20, the body 30 is freely rotatable relative to the bolt via means of the screw threads.

The body 30 has a slot or groove 34, the groove 34 having a base 35, two side walls 36, a top opening 37, and two side openings 38. The side walls 36 of the groove are substantially parallel with one another and planer. The spacing between the side walls 36 of the groove is slightly larger than the diameter of a spinal rod 40, such that a spinal rod can be received in the groove 34. The rotatable coupling of the body 30 on the bolt 20 allows the body 30 to be rotated relative to the installed bolt 20, to align the groove 34 with a spinal rod or a rod anchored to the bone.

Referring to FIG. 5D, the base 35 of the groove 34 is substantially triangular in cross-sectional shape, the base 35 having first and second faces 35a,35b inclining towards an apical centre-line 35c. The first and second faces of the base 35 are planar. The first face is angled at an angle A to a notional reference line X-X that is perpendicular to the longitudinal axis of the bolt in use (when the components are assembled). The second face is also angled at an angle A to the notional reference line X-X. Referring to FIGS. 7A and 7B, the angular alignment of the longitudinal axis of the spinal rod with respect to the reference line X-X can be varied by pivoting the rod about the apical centre-line of the base 35. The centre-line of the base therefore acts like a fulcrum of a see-saw. Referring to FIG. 7A, the rod has a first section 40a that is left of the base centre-line (or pivot line) of the base 35 when the rod is received in the groove, and a second section 40b that is right of the centre-line, as viewed in FIG. 7A. The rod 40 can pivot to any angle between a minimum angle, at which the first section 40a is at angle −A to the reference line X-X, and a maximum angle, at which the first section 40a is at angle +A to the reference line X-X. FIG. 7A shows the first section 40a of the rod close to the minimum angle, −A, to which the rod can pivot and FIG. 7B shows the rod close to the maximum angle, +A, to which the rod can pivot.

Preferably the first face 35a of the base 35 is angled at an angle of 40° to the reference line X-X and the second face 35b is also angled at an angle 40° to the reference line X-X, therefore the rod can be pivoted through a continuous range of angles, between a minimum angle of −40° to the reference line and a maximum angle of +40° to the reference line.

Alternatively the base 35 of the groove 34 can be convexly curved. The arched surface of the base 35 would be defined by a surface maximum extending along a centre line, between curved left and right side portions. Angular alignment of the longitudinal axis of the spinal rod with respect to the reference line would be varied by varying the point at which the rod contacts the base of the arched groove.

Figure 6:
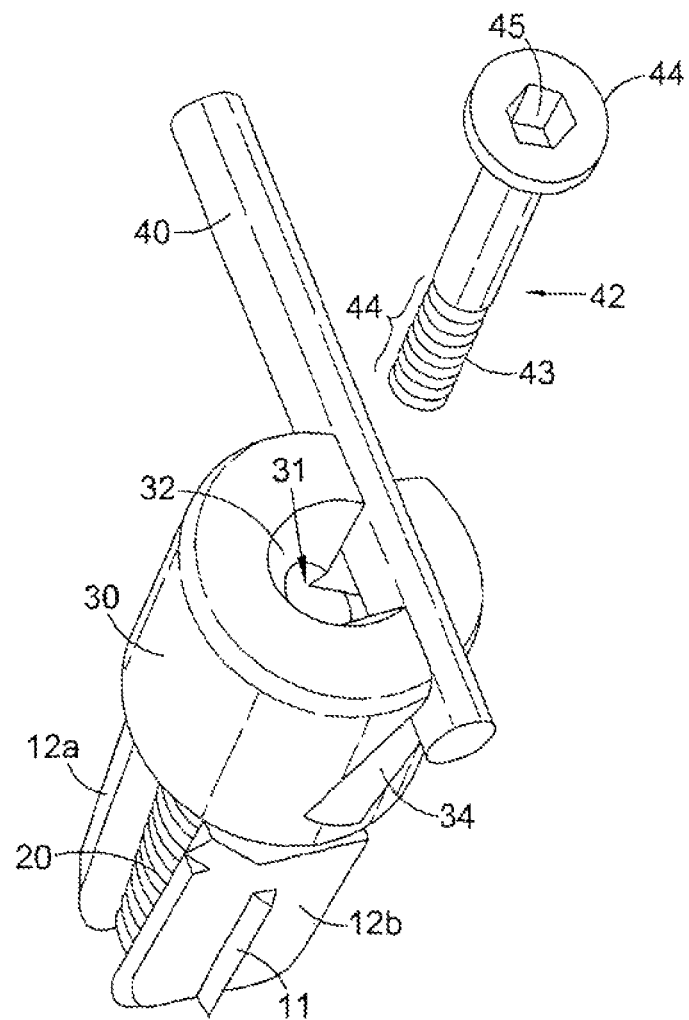
FIG. 6 is a top perspective view of an assembled spinal implant of FIG. 1, a spinal rod shown coupled to the implant and showing a locking screw exploded from the implant.

Referring to FIG. 6, the implant further comprises a locking screw 42. The locking screw 42 has a shank 43 and a head 44. The head 44 has a small bore having a first hexagonal shaped open end 45, into which can be received a hexagonal shaped key tool to be used to screw the locking screw 42 into the bolt 20. The shank 43 has a proximal portion 44 that is externally threaded. Referring to FIG. 3, bore 23 of bolt 20 has internal threads (not visible in the figures) that correspond to the external threads of the externally threaded proximal portion 44 of the locking screw shank. When the body 30 is assembled to the bolt 20, the shank of the locking screw 42 is receivable through the bore 31 of the body 30, and into the bore 23 of the bolt, such that the externally threaded proximal portion 44 engages with the internal threads of the bolt bore 23.

The head 44 of the locking screw has an underside that is tapered towards the screw shank. The first open end 32 of the bore 31 of the body 30 is countersunk in the shape of a conical recess, the conical recess matching the tapered shape of the underside of the screw head.

The bore 31 in the body 30 is aligned with the central longitudinal axis of the body 30. The bore 31 is adjacent the groove 34. The groove 34 is spaced from the bore 31 and the locking screw head 44 is sized such that when the locking screw 42 is received in the bore 31 of the body 30, the head 44 overlies at least part of the groove 34, such that a rod received in the groove 34 cannot be removed from the top opening of the groove 34. The angle of taper of the tapered portion of the screw head 44 is substantially the same, or is a few degrees greater, than angle A. When tightened, the screw head 44 produces pressurisation on the rod, thus clamping the rod against the body 30. This prevents the rod 40 from being removed from the top opening of the groove 34. The tightening of the locking screw 42 also locks the body 30 onto the bolt 20, and when the locking screw 42 is tightened, prevents the body 30 from rotating relative to the bolt 20.

In operation, in order to implant a spinal implant 10 in a subject's spine, the elongate body 13 is impacted between opposing vertebrae using an insertion tool as described above. The proximal end of the bolt 20 is introduced to the opening 18 of the elongate body 13, the proximal portion 22 of the bolt 20 engaging threadedly with the threaded portions 16 of the first and second plates. The bolt is rotated to threadedly screw the bolt between the first and second plates 12a, 12b, thus forcing the plates 12a, 12b apart and thus relieving pressure on any entrapped nerve. Rotation of the bolt between the first and second plates 12a, 12b causes relative movement of the whole of each plate away from the other plate. In this way, the spinal implant is a vertebral distractor for distracting adjoining vertebrae.

The body 30 is threadedly assembled to the distal portion 21 of the bolt 20. When initially assembled, the body 30 is freely rotatable relative to the bolt 20, such that the groove 34 for receiving a rod can be rotated to a desired rotational position about the longitudinal axis of the bolt. In this way the groove 34 can be rotated to align with the axis of a rod (wherein the rod may already be fixed elsewhere by other spinal implants according to the present invention, or other spinal fixings). The rod 40 is inserted in groove 34 and tilted on the triangulated base 35 of the groove 34, relative to the longitudinal axis of the bolt, to a desired angle. The locking screw 44 is inserted in the bore 32 of the body 30 and in the bore 23 of the bolt. This locks the body 30 to the bolt 20, preventing further rotation of the body relative to the bolt. Tightening of the locking screw also clamps the rod under the screw head, preventing the rod from being removed from the top opening of the groove 34.

The spinal implant assembly described above provides for rod misalignment relative to the longitudinal axis of the installed bolt 20 via rotation of the groove 34 about the bolt 20. The spinal implant assembly also provides elevational misalignment of the rod by means of pivoting of the rod to a desired angle relative to the longitudinal axis of the installed bolt 20 by means of the triangulated base in the groove. In this way, the rod can be aligned to any angle of alignment relative to the longitudinal axis of the bolt, and the rod can then be fixed at that angle of alignment by means of the locking screw.

When the locking screw 42 has been tightened such that a rod 40 received in the groove 34 is clamped against the body 30, the rod may still be rotated about, or slid translationally along, the rod's longitudinal axis, relative to the body 30. Referring to FIG. 1, two identical spinal implants can be used in combination. A single rod, received in the groove of the body of each spinal implant, couples the two spinal implants. Referring to FIG. 1, a first spinal implant can be impacted in an intervertebral disc at the right hand side of the disc, and a second spinal implant can be impacted in an intervertebral disc at the left hand side of the disc. A first part of the spinal rod can be received in the groove of the first spinal implant and another part of the spinal rod being received in the groove of the second spinal implant. By coupling the rod to a second implant, the rod is then rigidly held by the two implants, and the rod is no longer able rotate or slide translationally within the grooves of the implant bodies. An advantage of the spinal implant described is that first and second elongate bodies can be used to distract and fuse the left and right sides of an intervertebral disc. The first and second implants can be installed in the intervertebral disc on the left and right side of the disc, at divergent angles, avoiding bony protrusions extending over the intervertebral disc between the left and right sides; the spinal rod links and stabilises the spinal implants; the rod can be bent to avoid any bony protrusions that in its path. The spinal implants of the present invention therefore provide an improvement over large spinal implants, wherein a single implant is implanted in the inter-vertebral disc for distraction of opposing vertebrae.

The rod can be a part of a spinal rod system or it could be a short rod segment with an eyelet for attachment onto the adjacent bone; or the rod could form a bridge between similar devices elsewhere.

The thickness of each of the first and second plates 12a, 12b between the internal threaded surface and the external surface may increase towards the proximal end of each plate. The increase in thickness of the first and second plates 12a, 12b may be such that when the tapered, proximal portion 22 of the bolt 20 has been threadedly inserted between the first and second plates 12a, 12b, the external surfaces of the first and second plates 12a, 12b are parallel with one another. This provides parallel distraction of adjoining vertebrae.

Figure 8:
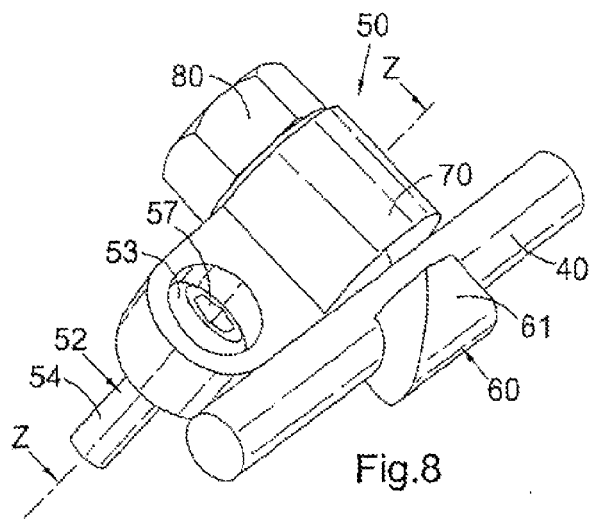
Figure 9:
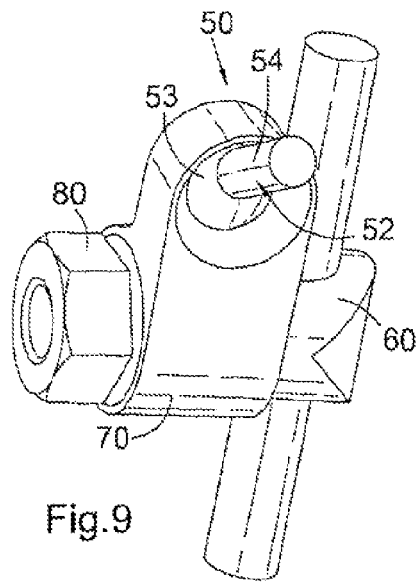

FIGS. 8 to 11 show an embodiment of a vertebral fixing 50. The vertebral fixing 50 has a fixing part 52 for fixing to part of a subject's spine, such as to a vertebra (not shown). The fixing part 52 is a bone screw having a head portion 53 and an extension portion 54. Only a portion of the extension portion 54 is shown in FIGS. 8 and 9. At least part of the extension portion 54 is externally threaded (threads not shown in the figures) for self-tapping fixation of the bone screw into vertebral bone. The head portion has a hexagonal shaped recess 57, allowing a hexagonal shaped key tool to be used to screw the fixing part into bone.

Referring to FIGS. 8 and 9, the vertebral fixing 50 further comprises a rod supporting component 60 and a coupling body 70. The coupling body 70 is for coupling together the fixing part 52 and the rod supporting component 60, in use. The rod supporting component has a hook 61 for receiving a rod 40 (only a portion of the rod is shown in the figures). The rod can be a metal spinal rod that is bendable to match the natural curvature of the spine. The vertebral fixing 50 is rigidly fixed to the spine in use via the fixing part 52, thus providing a rigid support to the rod 40, and therefore to the spinal column.

Figure 10:
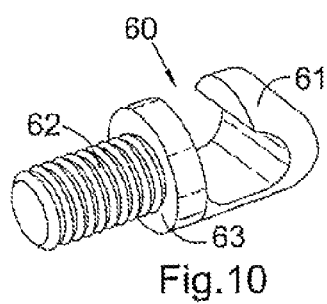

Referring to FIG. 10, the rod supporting component 60 has a shaft 62 at one end and the hook 61 at the other end. The hook 61 has a hooked end, the hooked end extending parallel to the axis of the shaft 62 in a retrograde manner. The hook 61 defines a channel in which the rod 40 can be received. The channel has a top opening and two side openings. The shaft 62 is elongate and is externally threaded.

Figure 11A:
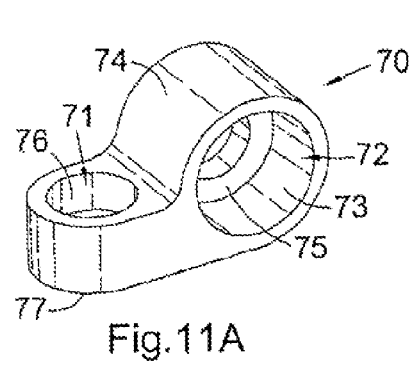
FIGS. 11A, 11B and 11C are perspective views of the coupling body of the vertebral fixing of FIG. 8.
Figure 11B:
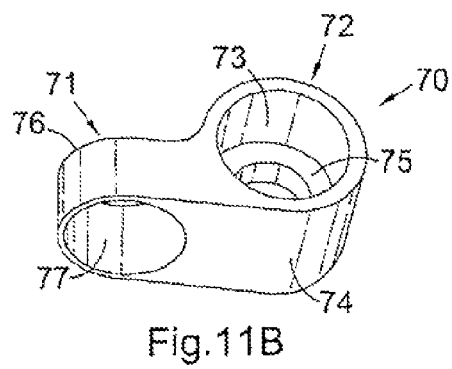
Figure 11C:
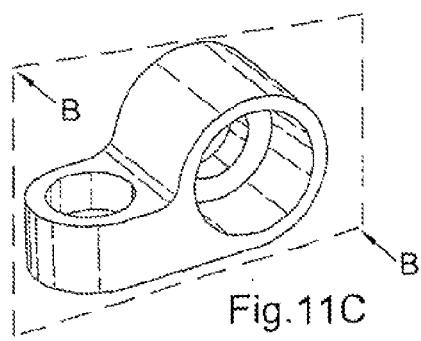
Figure 21:
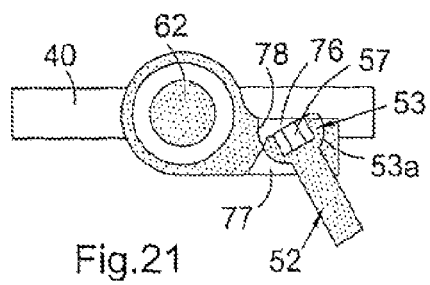

Referring to FIGS. 11A and 11B, the coupling body 70 comprises first bore 71, for receiving the fixing part 52 and a second bore 72, for receiving the shaft 62 of the rod supporting component. The longitudinal axes of the first and second bores 71, 72 are perpendicular to one another.

Referring to FIG. 8, the shaft 62 of the rod supporting component 60 is receivable in the second bore 72 of the coupling body 70. The diameter of the second bore 72 is large enough compared to the diameter of the shaft 62, such that the shaft 62 is rotatable within the bore 72 when inserted. The vertebral fixing further comprises a nut 80. The nut has an internally threaded bore, the internal threads of the nut corresponding to the external threads of the shaft 62, such that the nut 80 can be threadedly received on the shaft 62.

The second bore 72 has first and second open ends 73, 74. The shaft 62 of the rod supporting component is inserted in the second bore 72 via the first open end 73. The rod supporting component has a shoulder 63 at the base of the hook 61, which butts up against an internal shoulder 75 within the second bore 72 once the shaft 62 has been fully inserted.

The head portion 53 of the fixing part 52 is enlarged compared to the elongate extension portion 54. The underside 53a of the head portion 53 is rounded, like a partial sphere. The first bore 71 of the coupling body 70 has first and second open ends 76, 77. The end of the extension portion 54 of the fixing part 52 is inserted in the first bore 71 via the first open end 76, until the head portion 53 butts up against an internal shoulder 78 within the first bore 71. The shoulder 78 is rounded, the contour of the shoulder 78 corresponding with the rounded contour of the underside 53a of the head portion 53, such that the head portion 53 of the fixing part can pivot within the rounded socket defined by the shoulder 78, allowing the extension portion 54 to pivot relative to the coupling body.

The second open end 77 of the first bore 71 of the coupling body is funnel shaped or conically shaped; in other words the second open end 77 of the first bore 71 is a large circular opening, the walls of the bore narrowing towards a smaller diameter at a point along the longitudinal axis of the bore. This funnel shaped opening acts as a limiter to permit the extension portion 54 to pivot relative to the coupling body to a limited degree. The funnel shaped opening is configured such that the extension portion 54 can pivot by up to 40° in any direction relative to the longitudinal axis of the first bore 71.

Referring to FIG. 8, the vertebral fixing can be used to support a rod on the right hand side of the fixing part. A vertebral fixing wherein the coupling body is configured to support a rod on the left hand side of the fixing part can of course be provided; in this case, the coupling body will be a mirror image of the coupling body of FIG. 11C, in the mirror plane B-B.

In operation, to install the vertebral fixing, the fixing part 52, rod supporting component 60, coupling body 70, nut 80 and rod 40 will initially be separate from one another. The extension portion 54 of the fixing part 52 will be inserted through the first bore 71 of the coupling body. The fixing part 52 is then fixed to part of a subject's spine as described above. The head portion 53 can butt up against rounded internal shoulder 78 within the first bore 71. The rounded underside of the head portion 53 can pivot relative to the rounded internal shoulder 78 of the first bore 71, and the extension portion 54 is able to pivot relative to the coupling body 70, up to the angular alignment allowed by the funnel shaped opening 77. This allows the coupling body 50 to be pivoted to the desired angular alignment relative to the bone anchored fixing part 52.

The shaft 62 of the rod supporting component is inserted in the second bore 72 via the first open end 73 until the shoulder 63 of the rod supporting component buts up against the internal shoulder 75 of the second bore 72. The rod supporting component 60 can be rotated relative to the coupling body 70, such that the rotational alignment of the hook 61 relative to the coupling body (and therefore to the fixing part) can be varied, and the desired rotational alignment of the hook 61 selected by the installer. By means of rotation of the hook 61 relative to the coupling body 70, the hook 61 can be pivoted about the axis of the shaft 62, to vary the alignment of the longitudinal axis of the rod 40 (when received by the hook 61) as desired, relative to the fixing part 52. The rod 40 is inserted in the channel defined by the hook 61 via the top opening or by sliding the rod through the side openings of the channel. The hook 61 can be rotated relative to the coupling body 70 either before or after the rod 40 is received by the hook 61.

The nut 80 is threadedly engaged on the shaft 62 such that the coupling body 70 is on the shaft 62, and the coupling body is disposed between the nut and the rod 40. The nut 80 is tightened against the coupling body 70, pushing the coupling body 70 up against the rod 40, the longitudinal axis of the rod 40 running substantially perpendicular to the axis of the second bore 72 of the coupling body. The nut 80 is tightened until the coupling body 70 buts up fast against the rod 40, thus clamping the rod and locking it firmly in the hook 61. Once clamped, the rod 40 is held by an interference fit between the hook 61 and the coupling body 70, preventing the rod 40 from rotating about the longitudinal axis of the rod, moving slidingly within the channel of the hook 61, or from being removed from the top opening of the channel. The tightening of the nut 80 also prevents the rod supporting component 60 from rotating relative to the coupling body.

The vertebral fixing described accepts three-dimensional mismatch of the rod in relation to the adjacent pedicle screw. The direction of the extension portion 54 of the fixing part 52 can be angulated by up to 40° in any direction. The rod supporting component 60 is axially rotatable within the coupling body 70, and rod supporting component 60 allows a rod 40 to be captured within the hook receptacle 61 and locked with the nut 80, clamping the rod and locking it firmly. This arrangement allows three degrees of rotational alignment; the coupling body 60 is rotatable around and pivotable relative to the fixing part 52, the hook 61 is rotatable within the coupling body 70 (unless the rod is locked rigidly in place by tightening of the nut 80), and the rod is rotatable about its longitudinal axis. The vertebral fixing thus provides a large range of angular misalignment between the fixing part and the rod.

FIGS. 22 to 27 show an alternative embodiment of a vertebral fixing 250 like that shown in FIGS. 8 to 11. The embodiment of FIGS. 22 to 27 is very similar to the embodiment of FIGS. 8 to 11, except that the embodiment of FIGS. 22 to 27 includes means for captively retaining the rod supporting component against the coupling body in a first, unlocked configuration such that the rod supporting component is moveable relative thereto, yet captively retained. The embodiment of FIGS. 22 to 27 also includes means for locking the rod supporting component in a second, locked configuration, in which the rod supporting component is non-movably coupled relative to the coupling body, as will be described below.

Like the embodiment of FIGS. 8 to 11, the vertebral fixing 250 has a fixing part 252 for fixing to part of a subject's spine, such as to a vertebra (not shown). The fixing part 252 is a bone screw having a head portion 253 and an extension portion 254. At least part of the extension portion 254 may be externally threaded (threads not shown in the figures) for self-tapping fixation of the bone screw into vertebral bone. The head portion has a hexagonal shaped recess 257, allowing a hexagonal shaped key tool to be used to screw the fixing part into bone.

Figure 22:
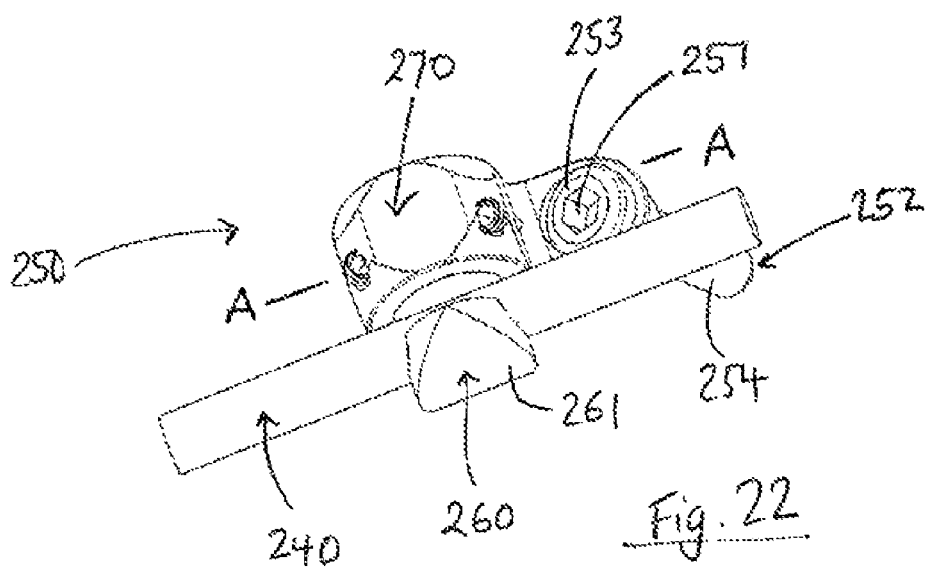
Figure 23:
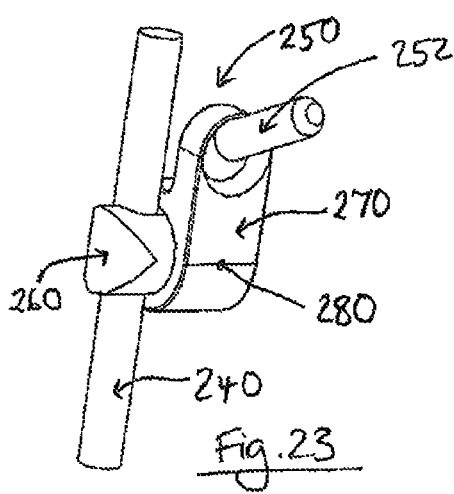

Referring to FIGS. 22 and 23, the vertebral fixing 250 further comprises a rod supporting component 260 and a coupling body 270. The coupling body 270 is for coupling together the fixing part 252 and the rod supporting component 260, in use. The rod supporting component has a hook 261 for receiving a rod 240 (only a portion of the rod is shown in the figures). The rod can be a metal spinal rod that is bendable to match the natural curvature of the spine. The vertebral fixing 250 is rigidly fixed to the spine in use via the fixing part 252, thus providing a rigid support to the rod 240, and therefore to the spinal column.

Figure 24A:
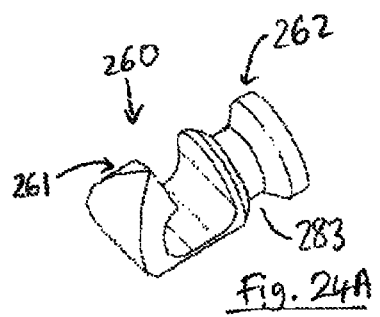
FIG. 24A is a side perspective view of the rod supporting component of the vertebral fixing of FIG. 22
Figure 24B:
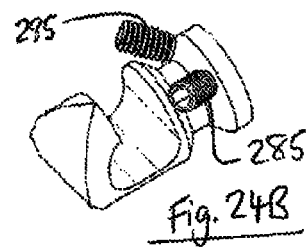
FIG. 24B is the side perspective view of the rod supporting component of FIG. 24A, but shown also with locking screws in position as they would be when received in bores in the coupling body, but with the coupling body not shown.

Referring to FIGS. 24A and 24B, the rod supporting component 260 has a shaft 262 at one end and the hook 261 at the other end. The hook 261 has a hooked end, the hooked end extending parallel to the axis of the shaft 262 in a retrograde manner. The hook 261 defines a channel in which the rod 240 can be received. The channel has a top opening and two side openings.

Figure 25A:
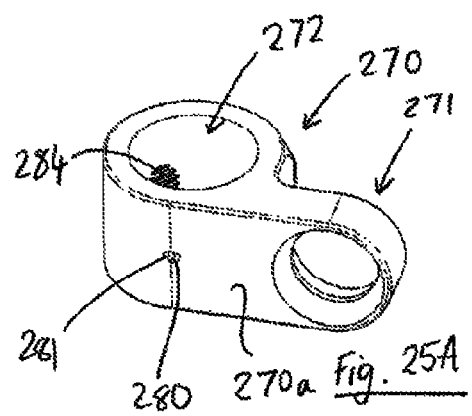
FIGS. 25A and 25B are perspective views of the coupling body of the vertebral fixing of FIG. 22.
Figure 27:
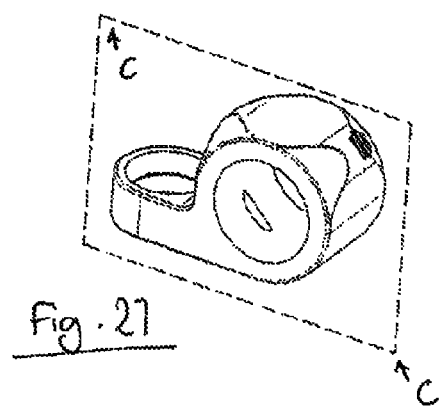
Figure 25B:
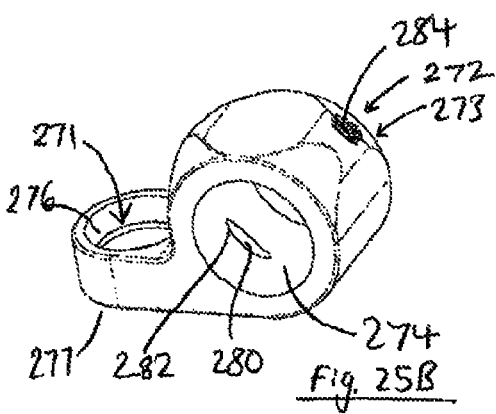

Referring to FIGS. 25A and 25B, the coupling body 270 comprises first bore 271, for receiving the fixing part 252 and a second bore 272, for receiving the shaft 262 of the rod supporting component. The longitudinal axes of the first and second bores 271, 272 are perpendicular to one another.

Figure 26:
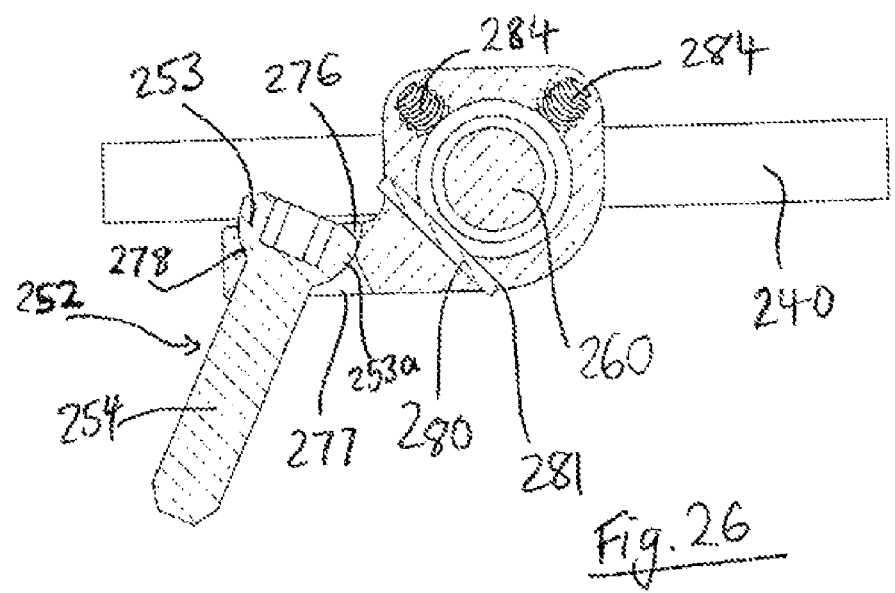

The shaft 262 of the rod supporting component 260 is receivable in the second bore 272 of the coupling body 270. The diameter of the second bore 72 is large enough compared to the diameter of the shaft 62, such that the shaft 62 is rotatable within the bore 72 when inserted. Referring to FIGS. 25A, 25B and 26, the vertebral fixing further comprises a retention pin 280 received in a pin receiving bore 281 that extends from the base 270a of the coupling body to a side of the coupling body, the pin receiving bore 281 having an opening 282 in the second bore 272 of the coupling body, such that the retention pin 280 protrudes into the second bore 272 when inserted. The pin 280 is visible protruding through opening 282 in FIG. 25B.

Referring to FIGS. 24A and 24B, the rod supporting component 260 has a groove 283 encircling the shaft 262. Referring to FIG. 26, the coupling body 270 has first and second threaded bores 284 for receiving first and second screws 285 respectively. Each of the first and second bores 284 has a first open end in the outer surface of the coupling body and a second open end in the inner surface of second bore 272. Each of the first and second screws 285 has a distal end having a hexagonal shaped recess (or other suitable shaped recess) allowing a corresponding shaped key tool to be used to drive the screw into the corresponding bore.

The second bore 272 has first and second open ends 273, 274. The shaft 262 of the rod supporting component is inserted in the second bore 272 via the first open end 273.

Referring to FIG. 26, as with the embodiment of FIGS. 8 to 11, the head portion 253 of the fixing part 252 is enlarged compared to the elongate extension portion 254. The underside 253a of the head portion 253 is rounded, like a partial sphere. The first bore 271 of the coupling body 270 has first and second open ends 276, 277. The end of the extension portion 254 of the fixing part 252 is inserted in the first bore 271 via the first open end 276, until the head portion 253 butts up against an internal shoulder 278 within the first bore 271. The shoulder 278 is rounded, the contour of the shoulder 278 corresponding with the rounded contour of the underside 253a of the head portion 253, such that the head portion 253 of the fixing part can pivot within the rounded socket defined by the shoulder 278, allowing the extension portion 254 to pivot relative to the coupling body.

The second open end 277 of the first bore 271 of the coupling body is funnel shaped or conically shaped; in other words the second open end 277 of the first bore 271 is a large circular opening, the walls of the bore narrowing towards a smaller diameter at a point along the longitudinal axis of the bore. This funnel shaped opening acts as a limiter to permit the extension portion 254 to pivot relative to the coupling body to a limited degree.

Referring to FIG. 22, the vertebral fixing can be used to support a rod on the right hand side of the fixing part. A vertebral fixing wherein the coupling body is configured to support a rod on the left hand side of the fixing part can of course be provided; in this case, the coupling body will be a mirror image of the coupling body of FIG. 27, in the mirror plane C-C.

In operation, to install the vertebral fixing, the rod supporting component 260 and coupling body 270 will be coupled together such that they form a single, unitary component. The vertebral fixing may be supplied to the installer with the rod supporting component 260 already coupled to the coupling body 270, the shaft 262 of the rod supporting component having been inserted in the second bore 272 of the coupling body via the first open end 273 and the retention pin 280 having then been inserted in the pin receiving bore 281. Once fully inserted in the pin receiving bore 281, the pin 280 is peened over at both ends to prevent it from moving out of the pin receiving bore 281. The retention pin 280 protrudes, via the opening 282, into the groove 283 in the shaft 262 of the rod supporting component. In this configuration the rod supporting component is captively retained to the coupling body, yet the rod supporting component is rotatably moveable with respect to the coupling body. The width of the groove 283 is wider than the diameter of the retention pin 280, therefore, the rod supporting component is also moveable translationally to a small extent back and forth within the second bore 272. Before installation of the vertebral fixing, the screws 285 can be inserted in their respective bores 284, but inserted only partway, such that their proximal ends do not abut against the base of the groove 283 in the rod supporting component 260, such that the rod supporting component is moveable relative to the coupling body 270.

The extension portion 254 of the fixing part 252 will be inserted through the first bore 271 of the coupling body. The fixing part 252 is then fixed to part of a subject's spine as described above. The head portion 253 can butt up against rounded internal shoulder 278 within the first bore 271. The rounded underside of the head portion 253 can pivot relative to the rounded internal shoulder 278 of the first bore 271, and the extension portion 254 is able to pivot relative to the coupling body 270, up to the angular alignment allowed by the funnel shaped opening 277. This allows the coupling body 250 to be pivoted to the desired angular alignment relative to the bone anchored fixing part 252.

The rod supporting component 260 can be rotated relative to the coupling body 270, such that the rotational alignment of the hook 261 relative to the coupling body (and therefore to the fixing part) can be varied, and the desired rotational alignment of the hook 261 selected by the installer. By means of rotation of the hook 261 relative to the coupling body 270, the hook 261 can be pivoted about the axis of the shaft 262, to vary the alignment of the longitudinal axis of the rod 240 (when received by the hook 261) as desired, relative to the fixing part 252. The rod 240 is inserted in the channel defined by the hook 261 via the top opening (or by sliding the rod through the side openings of the channel if desired). The hook 261 can be rotated relative to the coupling body 270 either before or after the rod 240 is received by the hook 261.

When the hook 261 is in the desired alignment relative to the fixing part 252 and the rod 240 has been inserted in the hook 261, the first and second screws 285 are tightened such that they extend further into their respective threaded bores 284, until the distal end of each screw 285 engages with the base of the groove 283. Tightening of the screws 285 rigidly fixes the rod supporting component against the coupling body, such that rod supporting component is non-movably fixed relative to the coupling body. Tightening of the screws 285 also pushes the coupling body 270 against the rod 240, thus clamping the rod 240 and locking it firmly within the hook 261. Once clamped, the rod 240 is held by an interference fit between the hook 261 and the coupling body 270, preventing the rod 240 from rotating about the longitudinal axis of the rod 240, moving slidingly within the channel of the hook 261, or from being removed from the top opening of the channel. In this locked configuration, the coupling body partly obstructs the longitudinal opening of the channel, preventing the rod 240 from being removed from the channel.

As with the embodiment of FIGS. 8 to 11, the vertebral fixing described accepts three-dimensional mismatch of the rod in relation to the adjacent pedicle screw. The direction of the extension portion 254 of the fixing part 252 can be angulated relative to the coupling body. The rod supporting component 260 is axially rotatable within the coupling body 270, and rod supporting component 260 allows a rod 240 to be captured within the hook receptacle 261 and locked using the screws 285, clamping the rod and locking it firmly. This arrangement allows three degrees of rotational alignment; the coupling body 260 is rotatable around and pivotable relative to the fixing part 252, the hook 261 is rotatable within the coupling body 270 (unless the rod is locked rigidly in place by tightening of the screws 285), and the rod is rotatable about its longitudinal axis. The vertebral fixing thus provides a large range of angular misalignment between the fixing part and the rod.

The captive arrangement of the rod supporting component within the coupling body, such that the rod supporting component is rotatable relative to the coupling body in a first configuration and non-movable relative to the coupling body when the vertebral fixing is in a second, locked configuration, means that the person installing the vertebral fixing only needs to assemble three parts when actually installing the vertebral fixing in a subject: fixing part 252, the unitary rod supporting component 260 within the coupling body 270 (including the retaining pin 280 and screws 285 inserted within their corresponding bores, and the rod 240.

Figure 12:
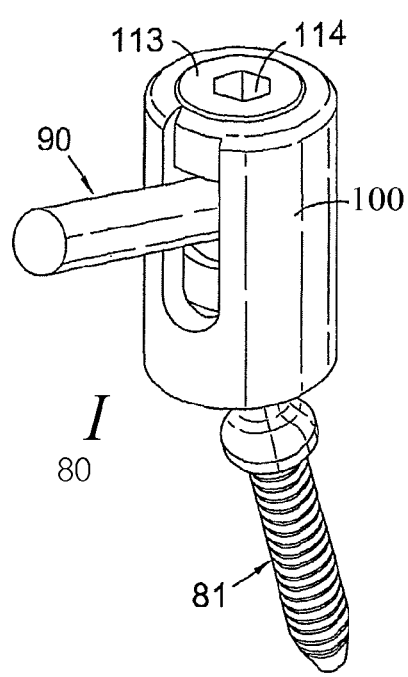
Figure 13:
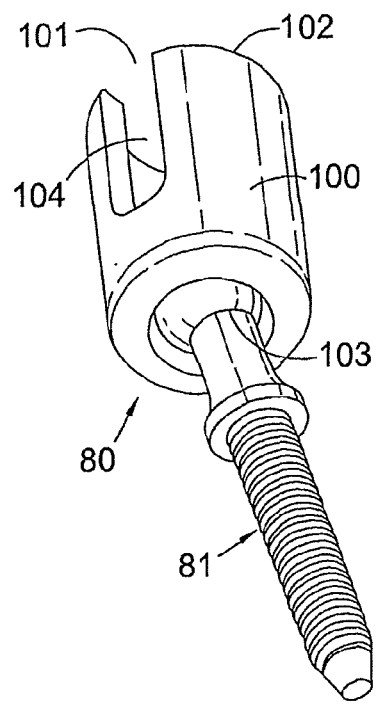

FIGS. 12 to 18 show an embodiment of another type of vertebral/spinal fixing 80. The spinal fixing 80 is a device for fusion of the lumbo-sacral joint. Referring to FIG. 12, the spinal fixing 80 has a fixing part 81 for fixing to part of a subject's spine, such as a vertebra or the sacrum, an elongate extension 90, and a coupling body 100 for receiving and coupling ends of the fixing part and elongate extension. The device is designed such that the fixing part 81 and elongate extension 90 are coupled for multi-axial position relative to the coupling body 100.

Figure 14:
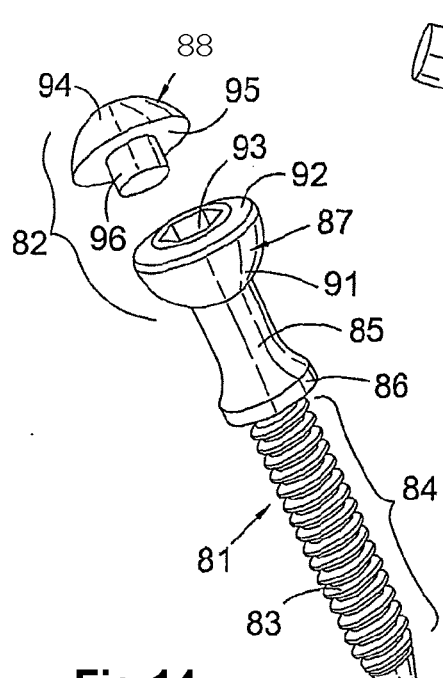

Referring to FIG. 14, the fixing part 81 is a bone screw, such as a pedicle screw for fixing in the pedicle of a vertebra. The fixing part 81 has a head portion 82 and a shank 83. The shank 83 has an externally threaded portion 84, for self-tapping fixation of the bone screw into the subject's bone. Between the head portion 82 and the threaded portion 84, the fixing part has an elongated neck portion 85. The elongated neck portion 85 is adjacent the head portion 82, and is not externally threaded. The elongated neck portion 85 has an enlarged shoulder 86 adjacent the threaded portion, the neck portion 85 tapering away from the enlarged shoulder 86 towards the head portion 82. The enlarged shoulder 86 may butt up against the bone surface when the tapered portion 84 has been implanted in the bone.

Alternatively the fixing part may include a hook that can be fixed to part of a spinal bone.

The head portion 82 of the fixing part comprises a part-spherical head part 87 and a removable rocker 88. The part-spherical head part is integral with or rigidly fixed to the shank 83 of the fixing part before assembly of the spinal fixing. The part-spherical head part has opposing first and second surfaces 91, 92. The first surface 91, faces towards the shank 83 of the fixing part, and is substantially hemispherical. The second surface 92 faces away from the shank 83 and is substantially planar; alternatively, the second surface 92 may have a slight curve. The second surface 92 includes a female recess 93. The recess 93 is hexagonal in shape. The recess 93 can receive a wrench or other torque-transferring tool, for transferring torque to the part-spherical head part during installation of the fixing part in the bone. Alternatively the recess 93 may be a shape other than hexagonal, the shape being suitable for receiving torque transfer from a suitable tool.

Figure 15:
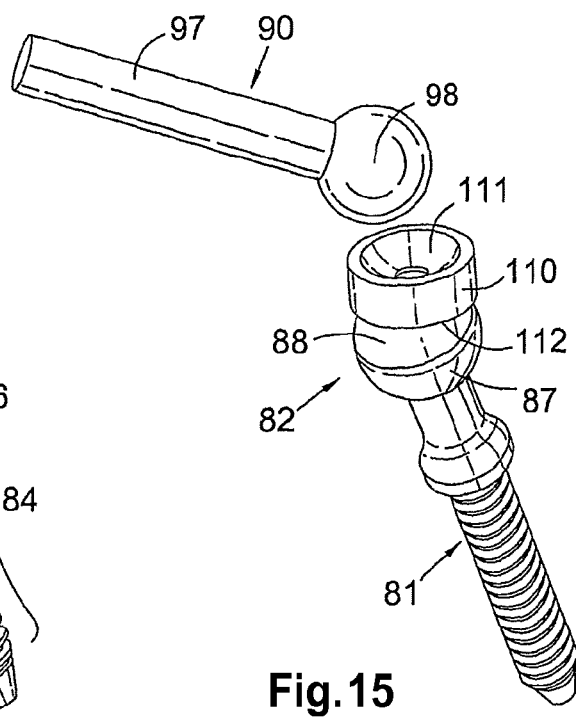

The removable rocker 88 has first and second opposing surfaces 94,95. The first surface 94 is substantially hemispherical. Alternatively, the first surface 94 may comprise the outer surface of a portion of a sphere that is less than or greater than hemispherical. The second surface 95 is substantially planar. A male protrusion or spigot 96 projects from the second surface 95. The male protrusion 96 is receivable in the female recess 93, such that the second surface 95 of the rocker 88 rests against the second surface 92 of the part-spherical head part 87 (see also FIG. 17). When the rocker 88 is assembled to the part-spherical head part 87 as described, the rocker 88 and part-spherical head part 87 form a substantially complete sphere, forming a substantially spherical ball end, comprising the head portion 82 on the fixing part 81. Referring to FIG. 15, the diameter of the rocker 88 is slightly less than the diameter of the part-spherical head part 87, however, when assembled together, the pieces 88 and 87 form a substantially complete sphere. In the embodiment shown in FIGS. 12 to 17, after placing the rocker 88 on the part-spherical head part 87, with the spigot 96 engaging in the recess 93, the rocker 88 is not rigidly affixed to the part-spherical head part 87; the rocker 88 and part-spherical head part 87 are simply held together in use by the other components of the device when assembled. Alternatively, the device may include means for rigidly fixing the rocker 88 to the part-spherical head part 87.

Referring to FIG. 15, the elongate extension 90 comprises a rod portion 97 having a ball end 98, the ball end being substantially spherical. The ball end 98 has a diameter that is substantially the same as that of the substantially spherical ball end of the head portion 82 of the fixing part.

Figure 16:
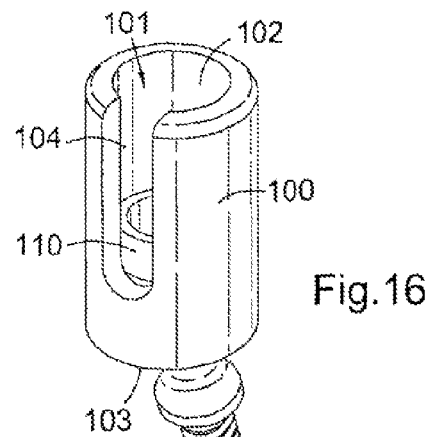
Figure 17:
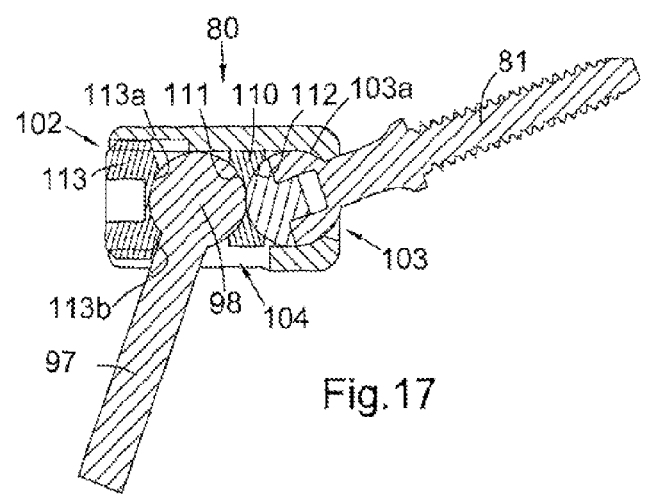

In FIGS. 12, 15 and 17, the elongate extension 90 is shown as having a short rod portion 97. The rod portion 97 may of course be long or short, and may be fixed to bone by another fixing device at the end of the rod remote from the ball end 98, and/or at one or more points along the length of the rod portion 97. The rod portion 97 may be straight of curved. The rod portion 97 may have a second ball end at the end remote from ball end 98, the second ball end being for coupling with a second spinal device as shown in FIGS. 12 to 17.

Referring to FIGS. 12, 16 and 17, the coupling body 100 comprises a tubular, hollow body. The coupling body 100 has a bore 101 having first and second open ends 102, 103. The second open end 103 has an opening that is circular in shape. The first open end 102 has an opening that is circular in shape, the circular opening communicating with an elongate slot 104 in the side of the coupling body 100. The elongate slot 104 extends from the first open end 102, part of the way down the side of the coupling body 100. The second open end 103 is smaller in diameter than the first open end 102. The first open end is large enough to receive the head portion 82 of the fixing part and the ball end 98 of the elongate extension therethrough. The opening of the second open end 103 is surrounded by a rounded edge 103a, internally to the coupling body. The curvature of the rounded edge 103a corresponds to the curvature of the head portion 82, such that the head portion 82 can pivot smoothly in the coupling body. Once assembled, the first surface 91 of the fixing part 81 butts up against the internal edge of the second open end 103.

The second open end 103 is funnel shaped or conically shaped. This funnel shaped opening acts as a limiter to permit the extension portion 97 to pivot relative to the coupling body to a limited degree. The funnel shaped opening is configured such that the fixing part 81 can pivot by up to 25° in any direction relative to the longitudinal axis of the bore 101.

The ball end 98 of the elongate extension is insertable through the first open end 102, so that the ball end 98 is received in the hollow of the coupling body 100 and the rod portion 97 extends out of the elongate slot 104.

The spinal fixing further comprises a washer 110, located in use between the head portion 82 of the fixing part and ball end 98 of the elongate extension. The washer 110 is generally cylindrical, having first and second opposing surface 111,112 (top and bottom surface), both of which are concavely curved. The curvature of the first and second opposing surface 111, 112 are the same, and correspond with the curvature of the ball end 98 of the elongate extension and the head portion 82 of the fixing part respectively. The intermediate conforming washer 110 increases the surface contact area that would exist between the ball end 98 of the elongate extension and the head portion 82 of the fixing part, if the washer were not present. The washer allows distribution of loads evenly between the ball end 98 of the elongate extension and the head portion 82 of the fixing part.

Referring to FIG. 12, the spinal fixing further comprises a locking screw 113, which acts as a compression member in use, to compress the ball end 98, washer 110 and head portion 82 together, against the inside of the coupling body 100, and therefore lock the angular orientation of the elongate extension 90 and fixing part 81 relative to the coupling body. The locking screw 113 has a circular cross-section, and has externally threaded sides. The coupling body 100 has internal threading on at least part of its internal surface, near to the first open end 102. The internal threads of the coupling body 100 correspond with the external threads of the locking screw 113. The locking screw 113 can be screwed into the first open end 102, thus providing a compressive force on the ball end 98, washer 110 and head portion 82. The locking screw 113 has hexagonal shaped recess in its top surface 114, which can receive a hexagonal shaped torque-transferring tool for tightening the locking screw in threaded engagement in bore 101. Alternatively the recess 114 may be a shape other than hexagonal, the shape being suitable for receiving torque transfer from a suitable tool.

Referring to FIG. 17, the underside of the locking screw 113 has a concavely curved surface 113a, the curvature of the concavely curved surface 113a corresponding with the curvature of the ball end 98 of the elongate extension. On the underside of the locking screw 113, surrounding the concavely curved surface 113a, is a chamfered surface 113b. The chamfered surface is angled such that, with the pieces of the spinal fixing assembled as shown in FIG. 17 (and with the locking screw loosely engaged in the bore 101), the elongate extension 90 can pivot relative to the coupling body 100 in the plane of the elongate slot 104, by up to 25° towards the second open end 103 and by up to 25° away from the first open end 103.

In operation, in order to assemble the spinal fixing and install it in a subject, the end of the fixing part remote from the head portion 82 is inserted, through the first open end 102, then through the second open end 103 of the bore 101 of the coupling body 100, until the first surface 91 of the fixing part 81 butts up against the internal edges of the second open end 103. A torque-transferring tool such as a wrench is received in the recess 93 in the second surface 92 of the part-spherical head part 87 to screw the fixing part 81 into the subject's bone. The rocker 88 is then located on the part-spherical head part 87, with the spigot 96 received in recess 93. The washer 110 is inserted in the coupling body 110, with the second surface 112 facing the rocker 88.

The ball end 98 of the elongate extension is insertable through the first open end 102 of the coupling body, so that the ball end 98 is received in the hollow of the coupling body 100 and the rod portion 97 extends out of the elongate slot 104. The ball end 98 rests against the concavely curved first surface 111 of the washer 110.

Once assembled as described above, the coupling body 100 can pivot relative to the bone-anchored fixing part 81 and the elongate extension 90 can pivot relative to the coupling body 100. As described above, the funnel shaped opening of the second open end 103 allows the fixing part 81 to pivot by up to 25° in any direction relative to the longitudinal axis of the bore 101. The elongate extension 90 can pivot about its ball end 98, within the confine of the elongate slot 104. If the locking screw 113 is loosely engaged in the coupling body 100, the elongate extension 90 can tilt by ±25° from a reference configuration at which the rod portion 97 extends perpendicular to the longitudinal axis of the bore 101. Accordingly, the angle between the longitudinal axes of the elongate extension 90 and the fixing part 81 can be varied between 40° and 130°, to allow optimal rod and screw placement.

The locking screw 113 can then be tightened within the threaded bore 101, to compress the ball end 98, washer 110 and head portion 82 together, against the inside of the coupling body 100. The locking screw 113 can be tightened until the elongate extension 90 and fixing part 81 are both locked pivotally, relative to the coupling body 100. Once the locking screw 113 is fully tightened, the elongate extension 90 and fixing part 81 are no longer able to pivot relative to the coupling body 100.

Figure 18A:
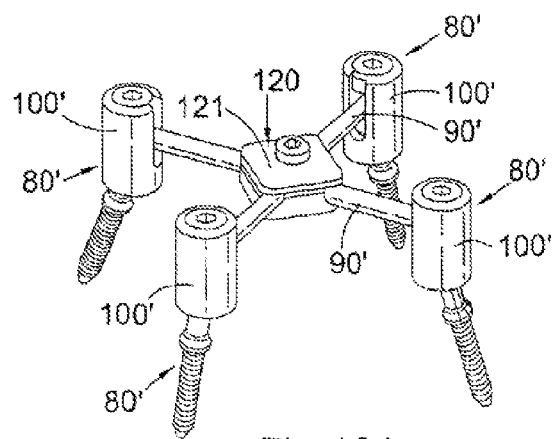
FIG. 18A is a perspective view of four spinal fixings of the type shown in FIG. 12 linked by two rods and a linker block.
Figure 18B:
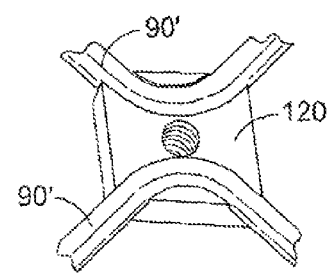
FIG. 18B shows a close-up view of the linker block without its cover.

The spinal fixing shown in FIGS. 12 to 17 is preferably used at the lumbo-sacral joint, for fusing the sacrum to the adjacent vertebra. Referring to FIGS. 18A and 18B, four spinal fixings 80' similar to that of FIG. 12 are shown. In the FIG. 18 embodiment, a single elongate extension 90' having two ball ends (the ball ends not visible in FIG. 18) and a bent mid-section is used to link two spinal fixings. Each elongate extension 90' has first and second ball ends, the first ball end being received in the coupling body 100' of a first spinal fixing and the second ball end being received in the coupling body 100' of a second spinal fixing, forming a linked pair of spinal fixings arranged side by side. A first linked pair of spinal fixings can be implanted in a subject's sacrum and a second linked pair of spinal fixings can be implanted above, in the subject's adjacent vertebra. In this way, the first and second linked pairs are arranged either side of the subject's lumbosacral joint. The first and second elongate extensions 90' are clamped together at their bent mid-sections using a suitable linker block 120. The linker block 120 has a cover 121. FIG. 18B shows the clamping of the first and second elongate extensions 90' using the linker block 120, with the cover 121 removed. This arrangement forms a cruciate bridge over the sacral joint, stabilising the joint.

FIGS. 28 to 32 show an alternative embodiment of a vertebral/spinal fixing 380 similar to that of the embodiment of FIGS. 12 to 17. The spinal fixing 380 differs from the embodiment of FIGS. 12 to 17 in that the curved faces of the washer 310 do not exactly conform to the corresponding spherical surfaces of the balls ends of the fixing part and elongate extension, as will be described below. Furthermore, the washer has a groove for allowing further range of movement of the elongate extension.

Referring to FIG. 30, the spinal fixing 380 has a fixing part 381 for fixing to part of a subject's spine, such as a vertebra or the sacrum, an elongate extension 390, and a coupling body 300 for receiving and coupling ends of the fixing part and elongate extension. The device is designed such that the fixing part 381 and elongate extension 390 are coupled for multi-axial position relative to the coupling body 300.

The fixing part 381 is a bone screw, such as a pedicle screw for fixing in the pedicle of a vertebra. The fixing part 381 has a head portion 382 and a shank 383. The shank 383 has an externally threaded portion 384, for self-tapping fixation of the bone screw into the subject's bone. Between the head portion 382 and the threaded portion 384, the fixing part has a neck portion 385. The neck portion 385 is adjacent the head portion 382, and is not externally threaded. The neck portion 385 has an enlarged shoulder 386 adjacent the threaded portion, the neck portion 385 tapering away from the enlarged shoulder 386 towards the head portion 382. The enlarged shoulder 386 may butt up against the bone surface when the threaded portion 384 has been implanted in the bone. Alternatively the fixing part may include a hook that can be fixed to part of a spinal bone.

The head portion 382 of the fixing part comprises a substantially spherical head part. The head portion 382 is integral with or rigidly fixed to the shank 383 of the fixing part before assembly of the spinal fixing. The head portion 382 includes a female recess 393. The recess 393 is hexagonal in shape. The recess 393 can receive a wrench or other torque-transferring tool, for transferring torque to the part-spherical head part during installation of the fixing part in the bone. Alternatively the recess 393 may be a shape other than hexagonal, the shape being suitable for receiving torque transfer from a suitable tool.

The elongate extension 390 comprises a rod portion 397 having a first ball end 398, the ball end being substantially spherical. The ball end 398 has a diameter that is substantially the same as that of the substantially spherical ball end of the head portion 382 of the fixing part.

In FIGS. 28 to 32 the elongate extension 390 is shown as having a second ball end 399 at the end remote from the first ball end 398. The rod portion 397 may of course be long or short, and may be fixed to bone by another fixing device at the end of the rod remote from the ball end 398, and/or at one or more points along the length of the rod portion 397.

The coupling body 300 comprises a tubular, hollow body. The coupling body 300 has a bore 301 having first and second open ends 302, 303. The second open end 303 has an opening that is circular in shape. The first open end 302 has an opening that is circular in shape, the circular opening communicating with an elongate slot 304 in the side of the coupling body 300. The elongate slot 304 extends from the first open end 302, part of the way down the side of the coupling body 300. The second open end 303 is smaller in diameter than the first open end 302. The first open end is large enough to receive the head portion 382 of the fixing part and the ball end 398 of the elongate extension therethrough. The opening of the second open end 303 is surrounded by a rounded edge 303a, internally to the coupling body. The curvature of the rounded edge 303a corresponds to the curvature of the head portion 382, such that the head portion 382 can pivot smoothly in the coupling body. Once assembled, the head portion 382 of the fixing part 381 buts up against the internal edge of the second open end 303.

The ball end 398 of the elongate extension is insertable through the first open end 302, so that the ball end 398 is received in the hollow of the coupling body 300 and the rod portion 397 extends out of the elongate slot 304.

Figure 28:
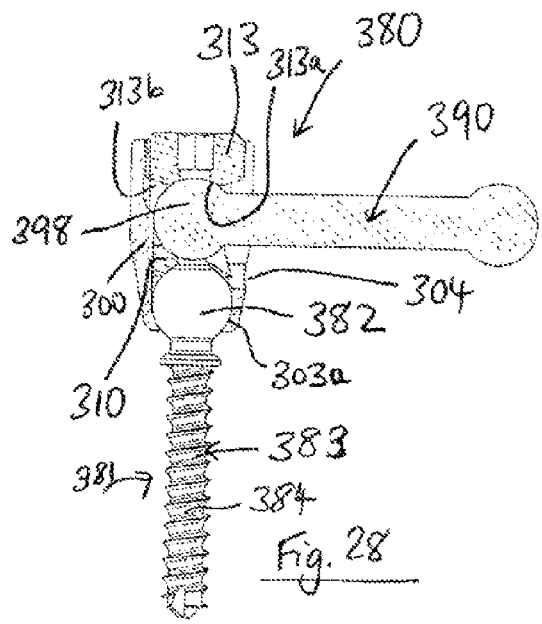
Figure 28B:
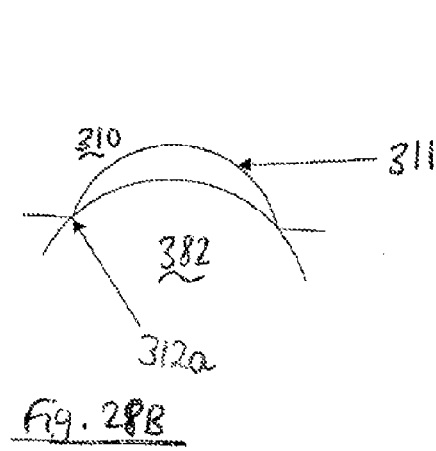
FIG. 28B is a diagrammatic view showing the contact line between the washer and the first end of the fixing part.
Figure 28A:
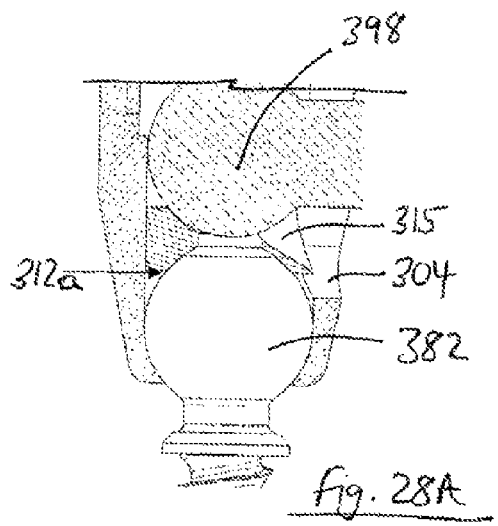
FIG. 28A is a close-up of the washer in the cross-sectional view of FIG. 28.

The spinal fixing further comprises a washer 310, located in use between the head portion 382 of the fixing part and ball end 398 of the elongate extension. The washer 310 is generally cylindrical, having first and second opposing surface 311,312 (top and bottom surface), both of which are concavely curved. The curvature of the first and second opposing surface 311,312 are substantially the same. Unlike the embodiment of FIGS. 12 to 18, the curvature of the first and second opposing surfaces 311, 312 of the washer 310 do not match the curvature of the ball end 398 of the elongate extension and the head portion 382 of the fixing part respectively. Instead, the radius of curvature of the first surface 311 of the washer is slightly less than the radius of curvature of the ball end 398 of the elongate extension. Similarly, the radius of curvature of the second surface 312 of the washer is slightly less than the radius of curvature of the spherical head part 382 of the fixing part. This non-conformance between the radius of curvature of each substantially spherical end part 382, 398 and the concave socket in the corresponding face of the washer 310 provides an edge contact between each substantially spherical end part 382, 398 and the corresponding edge of the washer 310. The presence of the washer 310 between the two substantially spherical end parts increases the contact that would exist between the ball end 398 of the elongate extension and the head portion 382 of the fixing part if the washer were not present and distributes loads evenly between the substantially spherical end parts. FIG. 28B shows diagrammatically an exaggerated version of the edge contact produced between the non-conformance of the curved surfaces of the second surface 312 of the washer and the substantially spherical head 382 of the fixing part, showing the edge 312a of the second surface of the washer that makes contact with the substantially spherical head portion 382 of the fixing part. The edge contact between the washer 310 and each substantially spherical spherical ball end 382, 298 comprises a circular line of contact, which enhances the locking mechanism provided by the washer.

Suitably, the radius of curvature of each surface of the first and second curved surfaces of the washer 310 may be around 0.5 mm less than the radius of curvature of the corresponding substantially spherical end parts 382, 398 of the fixing part and elongate extension. Taking into account manufacturing tolerances, such a difference in radius of curvature between the socket in the washer and the corresponding ball on the fixing part or elongate extension provides a line of contact between the two, providing a strong engagement when the pieces are forced against one another.

Referring to FIG. 30, the washer 310 has a notch 315 extending between the first surface 311 and the side of the washer. When assembled, the notch 315 faces towards the rod portion 397 of the elongate extension 390. Referring to FIG. 28, the notch allows for greater range of movement when the elongate extension 390 pivots within slot 304.

Referring to FIG. 30, the spinal fixing further comprises a locking screw 313, which acts as a compression member in use, to compress the ball end 398, washer 310 and head portion 382 together, against the inside of the coupling body 300, and therefore lock the angular orientation of the elongate extension 390 and fixing part 381 relative to the coupling body. The locking screw 313 has a circular cross-section, and has externally threaded sides (not visible in the figures). The coupling body 300 has internal threading on at least part of its internal surface, near to the first open end 302. The internal threads of the coupling body 300 correspond with the external threads of the locking screw 313. The locking screw 313 can be screwed into the first open end 302, thus providing a compressive force on the ball end 398, washer 310 and head portion 382. The locking screw 313 has a hexagonal shaped recess in its top surface 314, which can receive a hexagonal shaped torque-transferring tool for tightening the locking screw in threaded engagement in bore 301. Alternatively the recess 314 may be a shape other than hexagonal, the shape being suitable for receiving torque transfer from a suitable tool.

Referring to FIG. 28, the underside of the locking screw 313 has a concavely curved surface 313a, the curvature of the concavely curved surface 313a corresponding with the curvature of the ball end 398 of the elongate extension. On the underside of the locking screw 313, surrounding the concavely curved surface 313a, is a chamfered surface 313b, to allow a greater range of movement when the elongate extension 390 pivots relative to the coupling body 300 in the plane of the elongate slot 104.

In operation, in order to assemble the spinal fixing and install it in a subject, the end of the fixing part remote from the head portion 382 is inserted, through the first open end 302, then through the second open end 303 of the bore 301 of the coupling body 300, until the substantially spherical head part 382 of the fixing part 381 butts up against the internal edges of the second open end 103. A torque-transferring tool such as a wrench is received in the recess 393 of the substantially spherical head part 382 to screw the fixing part 381 into the subject's bone. The washer 310 is inserted in the coupling body 300, with the second surface 312 facing the head part 382 of the fixing part, and the notch facing the first bore 301. The washer 310 is rotated on top of the substantially spherical head part 382 of the fixing part 381 until the notch 315 faces the slot 304 in the coupling body 300.

The ball end 398 of the elongate extension is insertable through the first open end 302 of the coupling body, so that the ball end 398 is received in the hollow of the coupling body 300 and the rod portion 397 extends out of the elongate slot 304. The ball end 398 rests against the concavely curved first surface 311 of the washer 310.

Once assembled as described above, the coupling body 300 can pivot relative to the bone-anchored fixing part 381 and the elongate extension 390 can pivot relative to the coupling body 300. The elongate extension 390 can pivot about its ball end 398, within the confine of the elongate slot 304. Referring to FIG. 28, if the locking screw 313 is loosely engaged in the coupling body 300, the elongate extension 390 can tilt upwards (i.e. away from the fixing part) until the elongate extension abuts the chamfered surface 313b of the locking screw 313 and can downward (i.e. toward the fixing part) until the elongate extension 390 abuts the notch 315 in the washer 310 and/or the base of slot 304. The outer surface of the coupling body 300 tapers towards its second open end 303, allowing further range of movement of the elongate extension 390 relative to the coupling body 300 than the embodiment of FIGS. 12 to 18.

The locking screw 313 can then be tightened within the threaded bore 301, to compress the ball end 398, washer 310 and head portion 382 together, against the inside of the coupling body 300. The locking screw 313 can be tightened until the elongate extension 390 and fixing part 381 are both locked pivotally, relative to the coupling body 300. Once the locking screw 313 is fully tightened, the elongate extension 390 and fixing part 381 are no longer able to pivot relative to the coupling body 300.

Figure 29:
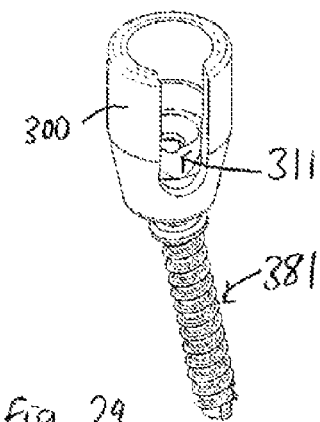

Referring to FIGS. 31 and 32, four spinal fixings 380' of FIGS. 28 to 30 are shown, similar to the assemblies of FIGS. 18A and 18B. In the FIGS. 31 and 32 embodiment, a single elongate extension 390' having two ball and a bent mid-section is used to link two spinal fixings. Each elongate extension 390' has first and second ball ends, the first ball end being received in the coupling body 300' of a first spinal fixing and the second ball end being received in the coupling body 300' of a second spinal fixing, forming a linked pair of spinal fixings arranged side by side. A first linked pair of spinal fixings can be implanted in a subject's sacrum and a second linked pair of spinal fixings can be implanted above, in the subject's adjacent vertebra. In this way, the first and second linked pairs are arranged either side of the subject's lumbo-sacral joint. As in the FIG. 18 embodiment, the first and second elongate extensions 390' are clamped together at their bent mid-sections using a suitable linker block 320. The linker block 320 has a cover 321. FIG. 31 shows the clamping of the first and second elongate extensions 390' using the linker block 320, with the cover 321 removed.

Figure 19:
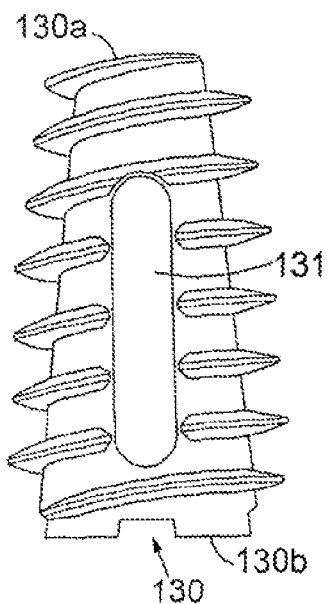
FIGS. 19 and 20 show another embodiment.
Figure 20:
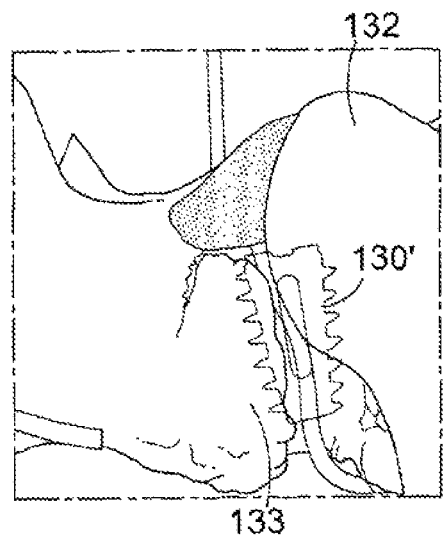

Referring to FIGS. 19 and 20, before stabilising the joint using a cruciate bridge as described above, it may be desirable to distract the lumbo-sacral joint. Referring to FIG. 19, a tapered bolt 130 is shown that can be used to induce fusion and distraction of the lumbo-sacral joint for the treatment of IVD disease in the region. The bolt 130 has a proximal end 130a and a distal end 130b, and is tapered towards the proximal end 130a. The external surface of the bolt is threaded with deep threads for cutting into bone. The threads are thin in section and very pronounced, to cut into the bone and aid the insertion process.

The bolt 130 is hollow. The proximal and distal ends 130a and 130b are open.

Alternatively, the proximal and distal ends 130a and 130b of the bolt may not be open.

The bolt has a first elongate slot 131, having a longitudinal axis running parallel with the longitudinal axis of the bolt 130. The bolt may have a second elongate slot opposite the first elongate slot 131. The bolt may have more than two elongate slots.

In operation, to install the bolt, the bolt is inserted at the lumbo-sacral joint, between the sacrum 132 and the adjacent vertebra 133, to wedge apart the bones. FIG. 20 shows a similar bolt 130' to that of FIG. 19, implanted between the sacrum 132 and the adjacent vertebra 133. The threads on the external surface of the bolt cut into the bone during insertion. The hollow internal section of the bone can be impregnated with bone graft before insertion of the bolt 130 in the bone. The subject's bone will ingrow, through the first elongate slot 131, and attach with the bone graft inside the hollow section of the bolt. This further anchors the bolt 130 in the subject, preventing the bolt from being rotated.

Even if no bone graft is inserted in the hollow of the bolt 130 before insertion of the bolt 20 into the subject's bone, cutting of the subject's bone by the bolt threads as the bolt is inserted will create bone debris that will accumulate, via the elongate slot(s) 131, in the hollow bore of the bolt 130. The subject's bone will ingrow, through the first elongate slot 131, and attach with the accumulated bone debris, further anchoring the bolt 130 against rotation.

Once the bolt 130 has been inserted into the bone at the lumbo-sacral joint, the cruciate bridge, as shown in FIG. 18, can be formed over the joint to stabilise the joint.

The outer surface of the bolt 130 may have a hydroxyapatite coating to stimulate bown ingrowth.

Figure 19A:
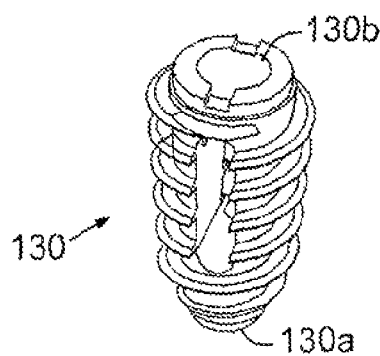
FIG. 19A is a top perspective view of a tapered bolt of FIG. 19.
Figure 19B:
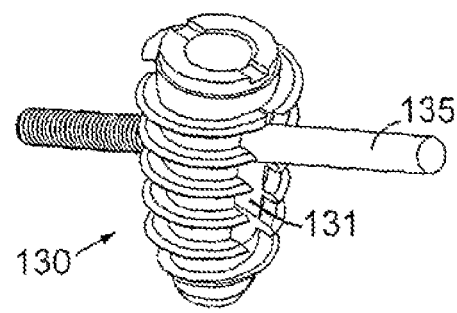
FIG. 19B is a top perspective view of a tapered bolt of FIG. 19, with an elongate locking pin inserted through the elongate slots.

Referring to FIG. 19B, the bolt 130 may be used with an elongate locking pin 135. Once the bolt 130 has been inserted at the lumbo-sacral joint, a locking pin 135 can be inserted through a first elongate slot 131 in the side of the bolt and out of a second elongate slot in the opposing side of the bolt (not visible in FIG. 19B) and into the adjacent bone. The locking pin 135 aids fixation and stabilises the bolt 130. At least a portion of the elongate pin 135 may be threaded to aid engagement in the adjacent bone.

It will be understood that a single spinal rod could be fixed to a subject's spine using one or more spinal implants according to the embodiment of FIG. 1 and one or more fixings according to the embodiment of FIG. 8 or 22. Similarly, a single spinal rod could be fixed to a subject's spine using one or more fixings according to the embodiment of FIG. 12 or 28 (the rod having at least one ball end) and one or more spinal implants according to the embodiment of FIG. 1 and/or one or more fixings according to the embodiment of FIG. 8 or 22. In this way, the implants/fixings shown in the figures could be used together as part of a single spinal system.

The invention claimed is:

1. A spinal fixing comprising
   a fixing part for fixing to a part of a subject's spine, the fixing part having a first end, the first end having a head that is at least partially spherical;
   an elongate extension, the elongate extension having a first end, the first end having a head that is at least partially spherical;
   a coupling body for receiving the first end of the fixing part and the first end of the elongate extension therein; and
   a washer located between the first end of the fixing part and the first end of the elongate extension in use, the washer having first and second opposing surfaces being concavely curved, the first surface facing the first end of the elongate extension in use and the second surface facing the first end of the fixing part in use, the radius of curvature of the first surface being smaller than the radius of curvature of the at least partially spherical end of the elongate extension such that the washer makes a circular line of contact with the first end of the elongate extension when the spinal fixing is assembled and the radius of curvature of the second surface being smaller than the radius of curvature of the at least partially spherical end of the fixing part such that the washer makes a circular line of contact with the first end of the fixing part when the spinal fixing is assembled.

2. A spinal fixing according to claim 1, wherein the spinal fixing further comprises a compression member for compressing the first end of the fixing part and the first end of the elongate extension in locking engagement within the coupling body.

3. A spinal fixing according to claim 2, wherein the compression member is a locking screw.

4. A spinal fixing according to claim 3, wherein at least part of the locking screw is externally threaded, the coupling body having a bore with first and second open ends, at least part of the bore being internally threaded, the internal threads of the bore corresponding with the external threads of the locking screw.

5. A spinal fixing according to claim 1, wherein the coupling body comprises a hollow tubular body, the first end of the fixing part and the first end of the elongate extension being receivable in the hollow tubular body in use.

6. A spinal fixing according to claim 1, wherein the first end of the fixing part is pivotally coupled to the coupling body in use, such that the fixing part can pivot relative to the coupling body over a pre-determined range of motion.

7. A spinal fixing according to claim 1, wherein the coupling body has a slot, the elongate extension extending through the slot in use, such that the elongate extension can pivot relative to the coupling body over a pre-determined range of motion.

8. A spinal fixing according to claim 7, wherein the slot is elongate, having a longitudinal axis perpendicular with the longitudinal axis of a bore of the coupling body.

9. A spinal fixing according to claim 1, wherein the first end of the fixing part comprises a part-spherical head part and a removable rocker, the part-spherical head part being integral with or rigidly fixed to the fixing part, the rocker having first and second opposing surfaces, the first surface being part-spherical, the rocker having a male protrusion projecting from the second surface, the part-spherical head having a female recess for receiving the male protrusion.

* * * * *